(12) United States Patent
Corbett et al.

(10) Patent No.: US 8,597,882 B2
(45) Date of Patent: Dec. 3, 2013

(54) METHOD AND APPARATUS FOR CONDUCTING AN ASSAY

(75) Inventors: John Corbett, Vaucluse (AU); John Corbett, Sr., Paradise Point (AU)

(73) Assignee: Pyrobett Pte. Ltd. (SG)

( * ) Notice: Subject to any disclaimer, the term of this patent is extended or adjusted under 35 U.S.C. 154(b) by 0 days.

(21) Appl. No.: 13/365,419

(22) Filed: Feb. 3, 2012

(65) Prior Publication Data

US 2013/0203049 A1  Aug. 8, 2013

(51) Int. Cl.
  *C12Q 1/68* (2006.01)
  *C12M 1/00* (2006.01)
  *C12M 1/34* (2006.01)
  *C07H 21/02* (2006.01)
  *C07H 21/04* (2006.01)

(52) U.S. Cl.
  USPC ..... 435/6.1; 435/283.1; 435/287.2; 536/23.1; 536/24.33

(58) Field of Classification Search
  USPC .......... 435/6.1, 283.1, 287.2; 536/23.1, 24.33
  See application file for complete search history.

(56) References Cited

U.S. PATENT DOCUMENTS

| | | | |
|---|---|---|---|
| 6,258,533 B1 * | 7/2001 | Jones | 435/6.18 |
| 6,319,469 B1 * | 11/2001 | Mian et al. | 422/64 |
| 8,080,410 B2 | 12/2011 | Corbett et al. | |
| 2004/0234970 A1 * | 11/2004 | Yoo | 435/6 |
| 2006/0223061 A1 * | 10/2006 | Corbett et al. | 435/6 |
| 2009/0325154 A1 * | 12/2009 | Ju et al. | 435/6 |
| 2010/0028978 A1 * | 2/2010 | Angros | 435/283.1 |
| 2010/0120599 A1 * | 5/2010 | Sarofim et al. | 494/37 |
| 2011/0009275 A1 | 1/2011 | Leamon et al. | |
| 2011/0124128 A1 * | 5/2011 | Oosterbroek et al. | 436/518 |
| 2011/0311980 A1 | 12/2011 | Pollack et al. | |

FOREIGN PATENT DOCUMENTS

| | | | |
|---|---|---|---|
| EP | 1324042 | | 7/2003 |
| WO | 98/49340 | | 11/1998 |
| WO | 2005/093388 | | 10/2005 |
| WO | WO2007/073107 | * | 6/2007 |
| WO | WO2010077859 | * | 7/2010 |

OTHER PUBLICATIONS

Zackrisson et al, Identification of CYP2D6 alleles by single nucleotide polymorphism analysis using pyrosequencing, 2003, Eur J Clin Pharmacol, 59, 521-526.*

Fakhrai-Rad et al, Pyrosequencing: An Accurate Detection Platform for Single Nucleotide Polymorphisms, 2002, Human Mutation, 19, 479-485.*

* cited by examiner

*Primary Examiner* — Narayan Bhat

(74) *Attorney, Agent, or Firm* — Roylance, Abrams, Berdo & Goodman, L.L.P.

(57) ABSTRACT

The present invention relates to methods and apparatus for conducting nucleic acid sequencing by pyrosequencing. The method comprises the steps of providing a platform having at least one well for containing at least one support surface, and providing at least one support surface within each well, wherein the support surface is adapted to immobilize a first binding partner or selectively immobilize a second binding partner. The method further comprises the steps of binding or immobilizing the first or second binding partner to the support surface and dispensing into each well from a point external of said platform a reagent, wherein after the dispensing step the platform is rotated sufficiently such that any residual or unreacted said reagent is substantially centrifugally removed from each well and/or each support surface, wherein during rotation each support surface is held within each well.

23 Claims, 17 Drawing Sheets

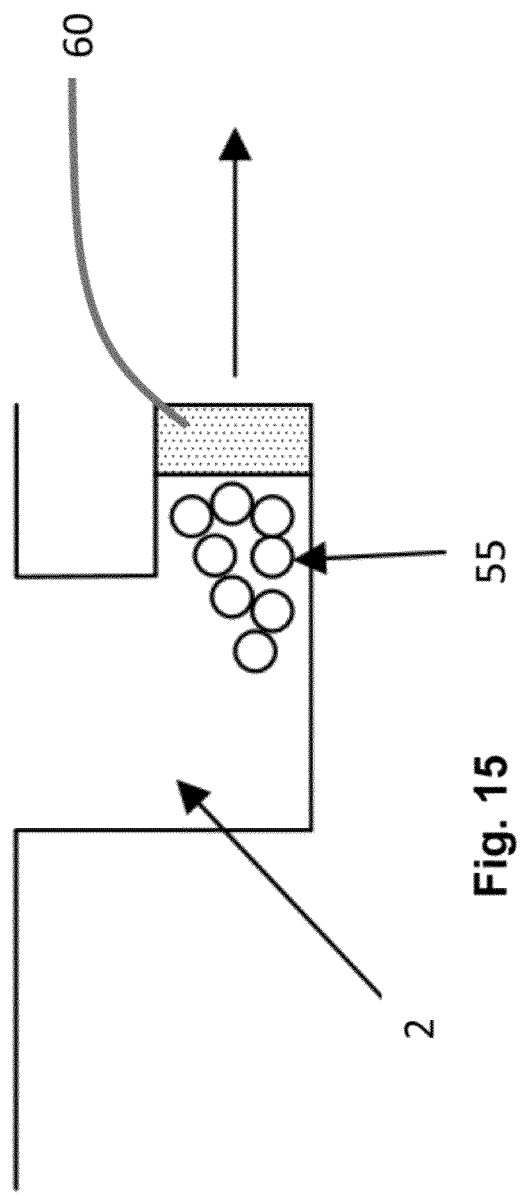

METHOD AND APPARATUS FOR CONDUCTING AN ASSAY

FIELD OF THE INVENTION

The present invention relates to a method and apparatus for conducting an assay. In particular, the present invention relates to a rotatable platform which can be used for conducting an assay, in particular multi-step assays. Whilst the invention has been developed primarily for use in sequencing nucleic acid by pyrosequencing, and will be described hereinafter with reference to this application, it will be appreciated that the invention is not limited to this particular field of use.

BACKGROUND OF THE INVENTION

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

The ability to determine DNA nucleotide sequences has become increasingly important in recent times. Previously, the two most commonly used methods for DNA sequencing are the enzymatic chain-termination method and the chemical cleavage technique, which both rely on gel electrophoresis to resolve, according to their size, DNA fragments produced from a larger DNA segment. The electrophoresis step and the detection of the separated DNA-fragments are cumbersome procedures. However, whilst automated electrophoresis units are commercially available, electrophoresis is not well suited for large-scale genome projects or clinical sequencing where relatively cost-effective units with high throughput are needed. Thus, the need for non-electrophoretic methods for sequencing is significant.

Methods of sequencing based on the concept of detecting inorganic pyrophosphate (PPi) which is released during a polymerase reaction have been described previously (see International PCT Publication No.'s WO 93/23564 and WO 89/09283) and commonly referred to as pyrosequencing. As each nucleotide is added to a growing nucleic acid strand during a polymerase reaction, a pyrophosphate molecule is released. It has been found that pyrophosphate released under these conditions can be detected enzymically e.g. by the generation of light in the luciferase-luciferin reaction. Such methods enable a base to be identified in a target position and DNA to be sequenced simply and rapidly whilst avoiding the need for electrophoresis and the use of harmful radiolabels.

Early prior art methods for conducting pyrosequencing employed a 0.2 mL microcentrifuge tube (or similar) with reagents being added to the tube sequentially to detect the sequence of the DNA present in the tube. Whilst this method is relatively simple, the method suffers from the drawback that the read lengths are short, since the reaction is diluted with each addition of nucleotide reagent and/or reaction by-products are accumulated and the reaction conditions reach a point where the reaction no longer proceeds. For example, typically only about 80 bases can be sequenced reliably with this method.

Commercial equipment which utilise pyrosequencing have also been developed. These systems use flow cells to perform hybridisation of a target DNA/RNA molecule. To explain, single-stranded DNA is immobilised on a stationary bead which is positioned in the flow cell, typically by immobilising a double-stranded DNA and denaturing the complementary strand. Reagents, including a nucleotide (A, G, C, or T) are flowed past the bead and light is detected if a nucleotide is incorporated. The signal strength of the light is proportional to the number of nucleotides incorporated in a single reaction. Between exposing the bead to different nucleotides a wash step is also performed and the process is repeated to detect incorporation of the next nucleotide.

Other methods of sequencing by synthesis are also known, for example by using fluorescently-labelled nucleotides. In such a method DNA samples are first fragmented and the DNA double-helix is melted into single strands. The single DNA molecules are captured on a surface within a flow cell and serve as templates for the sequencing-by-synthesis process. Fluorescently-labelled nucleotides are added one at a time and incorporated into the growing complementary strand by a DNA polymerase enzyme. Unused nucleotides are washed away. Upon illumination with a laser, the incorporated nucleotides emit light that is detected. The fluorescent label is removed before the next nucleotide is added to continue the cycle. Tracking nucleotide incorporation determines the exact sequence of each individual DNA molecule.

Sequencing by ligation is also known. This DNA sequencing method uses the enzyme DNA ligase to identify the nucleotide present at a given position in a DNA sequence. The mismatch sensitivity of a DNA ligase enzyme is used to determine the underlying sequence of the target DNA molecule. See for example U.S. Pat. No. 5,750,341 and U.S. Pat. No. 4,883,750.

What is needed is apparatus for conducting assays and analyses, which can be used with a variety of chemistries and detection methods, and in particular for conducting assays that involve multiple reaction and washing steps such as used in sequencing nucleic acid. Further, what is needed is apparatus which can be used as a convenient replacement for assays which require a flow-through environment, or to replace fixed reaction vessel assays where, in case of nucleic acid sequencing, build up of by-products can limit the maximum sequencing read length.

It is an object of the present invention to overcome or ameliorate at least one of the disadvantages of the abovementioned prior art, or to provide a useful alternative.

SUMMARY OF THE INVENTION

The present invention relates to a method of using a rotatable platform having at least one well for containing a support surface, and loading at least one support surface into each well. The support surface is adapted to bind or immobilise a first or a second binding partner of a first and second binding partner pair. The first and second binding pairs are part of an assay, which assay is preferably sequencing of nucleic acid, and is more preferably pyrosequencing. Reagents for the assay are dispensed into the well and into contact with the support surface from a point external of the platform. The used or spent reagents can be centrifugally removed by sufficient rotation of the platform, and the support surfaces are retained in the well during centrifugation. Any method of retaining the support surfaces falls within the purview of the present invention, and by way of example only, the support surfaces are preferably magnetic beads, and a magnet is used to retain magnetic beads in the wells during centrifugation. In the context of pyrosequencing, preferably the single stranded DNA (ssDNA) is isolated by centrifugal washing approach. The reagents may be removed after each new addition of reagent, or after multiple additions. The centrifugal washing step dries the support surface and prepares it for a subsequent reagent, and also removes unwanted by-products from the assay. The present invention also relates to apparatus for rotating the platform and holding the support surface within a respective well, and kits comprising a platform and support surface.

According to a first aspect, the present invention provides a method for conducting nucleic acid sequencing, said method comprising the steps of:
  providing a platform having at least one well for containing at least one support surface;
  providing at least one said support surface within each said well, wherein said support surface is adapted to immobilise a first binding partner;
  binding or immobilising said first binding partner to said support surface; and
  dispensing a reagent into each said well from a point external of said platform, wherein after said dispensing step said platform is rotated sufficiently such that any residual or unreacted said reagent is substantially centrifugally removed from each said well and/or each said support surface,
  wherein during rotation each said support surface is held within each said well.

Preferably the nucleic acid sequencing is pyrosequencing.

Preferably the support surface is in the form of a magnetic particle and said magnetic particle is magnetically held within said well by positioning a magnet sufficiently close to said platform to magnetically hold said magnetic particle(s) within said well during rotation of said platform. Preferably the magnet is in the form of a plate or a ring which sits underneath the platform. In preferred embodiments the magnetic plate or ring is further adapted to heat said well(s) up to about 150° C., thereby heating said support surface. However in an alternative embodiment an electromagnet is engaged to magnetically hold said magnetic particle(s) within said well during rotation of said platform.

In preferred embodiments the platform is substantially circular and said wells are distributed about the periphery of said circular platform. Preferably about 2 to 500 wells are distributed about the periphery of said platform, and the diameter of said platform is between about 50 to 500 mm and the thickness of said platform is about 1 to 6 mm. Preferably the wells comprise a volume of between about 0.5 to 100 μL or a well depth of about 0.5 to 5 mm. Preferably the wells are dimensioned to contain between about 1 to about 50 discrete support surfaces.

In an alternative embodiment, the well includes a recess for receiving said support surface during rotation of said platform, wherein said recess includes a filter adapted to retain said support surface but let said reagent pass therethrough during rotation of said platform such that any residual or unreacted said reagent is substantially centrifugally removed from each said well and/or each said support surface.

Preferably the platform is formed of a plastics material selected from the group consisting of polycarbonate, polystyrene, high impact polystyrene, polyethylene and polypropylene, or is formed from glass or quartz. Preferably a trough is disposed at the periphery of said platform for receiving waste fluids which are spun off or centrifuged away from said platform during rotation.

Preferably the first binding partner is chemically adsorbed or covalently or ionically, or hydrogen bonded onto said support surface, or van der Waals forces immobilise said first binding partner to said support surface.

Preferably a series of reagents are dispensed into each said well, and the first of the series of reagents comprises the second binding partner to the first binding partner, and the subsequent reagents are chosen from washing and/or rinsing reagents and reagents for developing a detectable signal. Preferably the method of the invention further comprises the step of analysing the nucleic acid sequencing during and/or after each said dispensing step.

Preferably the method of the invention further comprises the step of rotating the rotatable platform at a speed of between about 10 to 200 rpm whilst dispensing said reagent, and rotating the rotatable platform at a speed of greater than 400 rpm to substantially centrifugally remove said reagent from said wells. Preferably the platform is rotated at a sufficiently low speed such that no reagent is centrifugally removed from the wells during the dispensing steps, and rotated at a sufficiently high speed such that reagent is centrifugally removed from the wells during the washing or drying steps. Preferably the sufficiently high speed is greater than 400 rpm, and may be 1000, 2000, 3000, 4000 rpm or higher.

In some preferred embodiments the platform is vibrated sufficiently to thoroughly mix together said reagent and said support surface(s).

According to a second aspect the present invention provides a kit comprising a platform having at least one well for containing one or more support surfaces, and at least one support surface in the kit, wherein said support surface is adapted to immobilise a first binding partner.

Preferably the support surface is contained in said well and wherein a removable disposable sheet is adhered to the surface of said platform for retaining said support surface in said well. Preferably the kit comprises one or more reagents for conducting nucleic acid sequencing, and in particular for pyrosequencing.

According to a third aspect the present invention provides apparatus for conducting nucleic acid sequencing, said apparatus comprising:
  apparatus for rotating a rotatable platform at a predetermined controllable user-selectable rotational speed;
  apparatus for engaging a magnet to said rotatable platform for retaining a magnetic particle within a well of said platform;
  optionally apparatus for dispensing a first binding partner into said well for immobilising said first binding partner to said magnetic particle;
  apparatus for dispensing a reagent into said well; and
  optionally apparatus for dispensing a washing reagent.

According to a fourth aspect the present invention provides a method for conducting nucleic acid sequencing, said method comprising the steps of:
  providing a platform having at least one well for containing at least one support surface;
  providing at least one said support surface within each said well, wherein said support surface is adapted to immobilise a second binding partner;
  selectively binding or immobilising said second binding partner to said support area; and
  dispensing a reagent into each said well from a point external of said platform, wherein after said dispensing step said platform is rotated sufficiently such that any residual or unreacted said reagent is substantially centrifugally removed from each said well and/or each said support surface,
  wherein during rotation each said support surface is held within each said well.

Preferably a first binding partner is already chemically adsorbed or covalently or ionically, or hydrogen bonded onto said support surface, or van der Waals forces immobilise a first binding partner to said support surface, and said second binding partner is bindable or reactable to said first binding partner already bound to said support surface.

Preferably a series of reagents are dispensed into each said well, and the first of the series of reagents comprises the second binding partner to the first binding partner, and the subsequent reagents are chosen from washing and/or rinsing reagents.

According to a fifth aspect the present invention provides a kit comprising a platform having at least one well for containing one or more support surfaces, and at least one support surface, wherein said support surface is adapted to selectively bind or immobilise a second binding partner.

According to a sixth aspect the present invention provides apparatus for conducting nucleic acid sequencing, such as pyrosequencing, said apparatus comprising:
 apparatus for rotating a rotatable platform at a predetermined controllable user-selectable rotational speed;
 apparatus for engaging a magnet to said rotatable platform for retaining a magnetic particle within a well of said platform;
 optionally apparatus for dispensing said second binding partner into said well for selectively immobilising said second binding partner to said magnetic particle;
 apparatus for dispensing a reagent into said well; and
 optionally apparatus for dispensing a washing reagent.

According to a seventh aspect the present invention provides a method for conducting sequencing of a nucleic acid strand, said method comprising the steps of:
 providing a platform having at least one well for containing at least one support surface;
 providing at least one said support surface within each said well, wherein said support surface is adapted to immobilise a nucleic acid strand binding partner;
 binding or immobilising said nucleic acid strand binding partner to said support surface and then selectively binding or immobilising a nucleic acid strand to said support surface;
 optionally denaturing and removing any complementary nucleic acid strand, annealing a sequencing primer to said support surface; and
 sequentially dispensing into each said well from a point external of said platform a series of reagents comprising A, T, G and/or C nucleotides or the respective suitable nucleotide analogs, wherein after each or any of said dispensing step said platform is rotated sufficiently such that substantially any residual or unreacted said reagent is substantially centrifugally removed from each said well and/or each said support surface,
 wherein during rotation each said support surface is held within each said well.

Preferably the nucleic acid strand is DNA or RNA or a modified form thereof. Preferably the sequencing of a nucleic acid strand is pyrosequencing.

Preferably the nucleic acid strand is biotinylated and the nucleic acid strand binding partner comprises avidin or streptavidin or an analogue for binding the biotinylated nucleic acid strand.

Preferably each said support surface is contacted sequentially with a series of reagents comprising A, T, G and/or C nucleotides.

Preferably the sequential contacting/dispensing step comprises either:
 a.) each nucleotide or its analog is added separately and sequentially in any desired or predetermined order,
 b.) A+T+G+C nucleotides or any predetermined or desired subset of these are added as a mixture, and the mixture added again, etc.

Preferably further comprising the step of analysing said nucleic acid strand during and/or after each said dispensing step. Preferably the analysis comprises detecting the next base pair in said nucleic acid strand by correlating the output of light with the number of nucleotides which have become bound to the nucleic acid strand.

Preferably the denaturing step comprises heating the nucleic acid strand to effect denaturing, or exposing the nucleic acid strand to elevated pH.

Preferably the method comprises the step of wherein after said nucleic acid strand is denatured the complementary strand is removed by a rinse step with a rinsing reagent.

Preferably each said support surface is prepared for each said subsequent reagent by substantially drying said support surface by rotation of said platform to substantially centrifugally remove any residual reagents such that there is substantially no contamination of said support surface with a reagent.

According to an eighth aspect the present invention provides a kit for conducting sequencing of a nucleic acid strand, said kit comprising a rotatable platform having at least one well for containing one or more support surfaces, and at least one support surface, wherein said support surface is adapted to immobilise a nucleic acid strand binding partner.

According to a ninth aspect the present invention provides use of the kit according to the eighth aspect for conducting sequencing of a nucleic acid strand. Preferably the assay is pyrosequencing.

According to a tenth aspect the present invention provides apparatus for sequencing a nucleic acid strand, said apparatus comprising:
 apparatus for rotating a rotatable platform at a predetermined controllable user-selectable rotational speed;
 apparatus for engaging a magnet to said rotatable platform for retaining a magnetic particle within a well of said rotatable platform;
 optionally apparatus for dispensing a nucleic acid strand binding partner into said well for immobilising said nucleic acid strand binding partner to said magnetic particle;
 optionally apparatus for dispensing a nucleic acid strand into said well for selectively immobilising said nucleic acid strand to said magnetic particle;
 optionally apparatus for denaturing and optionally removing any complementary nucleic acid strand;
 apparatus for dispensing A, T, G and/or C nucleotides or their respective analogs or combinations thereof into said well;
 apparatus for dispensing a washing reagent; and
 optionally an apparatus for dispensing one or more enzyme solutions.

According to an eleventh aspect the present invention provides a method for conducting sequencing of a nucleic acid strand, said method comprising the steps of:
 providing a platform having at least one well for containing at least one support surface;
 providing at least one said support surface within each said well, wherein said support surface is adapted to selectively immobilise a nucleic acid strand;
 selectively binding or immobilising a nucleic acid strand to said support surface;
 optionally denaturing and removing any complementary nucleic acid strand, annealing a sequencing primer to said support surface; and sequentially dispensing into each said well from a point external of said platform a series of reagents comprising A, T, G and/or C nucleotides or the respective suitable nucleotide analogs, wherein after each or any of said dispensing steps said platform is rotated sufficiently such that any residual or unreacted said reagent is substantially centrifugally removed from each said well and/or each said support surface, wherein during rotation each said support surface is held within each said well.

Preferably the support surface already has immobilised thereto a nucleic acid strand binding partner, and wherein said nucleic acid strand selectively binds to said nucleic acid strand binding partner. Preferably the nucleic acid strand is DNA or RNA or a modified form thereof. Preferably the nucleic acid strand is biotinylated and the first binding partner comprises avidin or streptavidin or an analogue for binding the biotinylated nucleic acid strand.

According to a twelfth aspect the present invention provides a kit comprising a rotatable platform having at least one well for containing one or more support surfaces, and at least one support surface, wherein said support surface is adapted to selectively immobilise a nucleic acid strand.

According to a thirteenth aspect the present invention provides use of the kit according to the twelfth aspect for conducting sequencing of a nucleic acid strand.

According to a fourteenth aspect the present invention provides apparatus for sequencing a nucleic acid strand, said apparatus comprising:

apparatus for rotating a rotatable platform at a predetermined controllable user-selectable rotational speed;

apparatus for engaging a magnet to said rotatable platform for retaining a magnetic particle within a well of said rotatable platform;

optionally apparatus for dispensing a nucleic acid strand into said well for immobilising said nucleic acid strand to said support surface;

optionally apparatus for denaturing and optionally removing any complementary nucleic acid strand;

apparatus for dispensing A, T, G and/or C nucleotides or their respective analogs or combinations thereof into contact with said support surface;

apparatus for dispensing a washing reagent; and optionally an apparatus for dispensing one or more enzyme solutions.

In some embodiments the rotatable platform comprises a plurality of relatively shallow wells which comprise a volume of between about 0.5 to 100 µL or a well depth of about 0.5 to 3 mm. In other embodiments, the wells are relatively deep, at about 5 to 8 mm for containing magnetic beads which themselves are adapted to immobilise a first binding partner or adapted to selectively immobilise a second binding partner. In this example, the beads are considered as discrete areas, and one or more beads may be contained in each well.

The first or second binding partners are preferably bindable to beads, which are preferably magnetic beads. It will be appreciated that if magnetic beads are employed that the well is of a sufficient depth and volume to contain the beads such that they are not centrifugally displaced during rotation of the disc/platform. In preferred embodiments, the system has the capability to capture magnetic beads within each of the wells by raising a magnetic annular disc to the under-side of the sample disc/platform, or activating an electromagnet. In this example the magnetic beads can be contained in the wells and sufficient centrifugal force can be applied by rotation of the platform to substantially dry the beads from any surrounding reagent. It will also be appreciated that the platform may comprise a plurality of concentrically positioned circular arrays of wells.

In some embodiments, the first binding partner is chemically adsorbed on the surface of the bead or particle. In other embodiments, the first binding partner is covalently or ionically or hydrogen bonded to the surface of the bead or particle, and in yet other embodiments van der Waals forces hold the first binding partner to the surface of the bead or particle. It will be appreciated that the second binding partner is bindable or reactable to the first binding partner already bound to the surface of the bead or particle.

The present invention is particularly relevant to methods and assays such as nucleic acid sequencing methods, for example pyrosequencing. For example, the first and second binding partners are binding partner pairs (optionally one of which may be detectably labelled), which are preferably selected from avidin or streptavidin or streptactin or analogs and biotin or analogs.

However, and as discussed further below, an advantage of the present invention is to provide relatively fast and relatively simple washing steps, and associated low waste volumes of washing solution and reagents.

The present invention will now be explained in the context of pyrosequencing, however it will be appreciated that the invention is not limited to this assay.

It will be appreciated that in a first embodiment the support surface held within the well is adapted to immobilise a first binding partner, which may be for example avidin or streptavidin or streptactin or analogs, and then the avidin or streptavidin or streptactin or analogs can be subsequently reacted with say, biotinylated DNAs, in a subsequent processing step. It will be further appreciated that in a second embodiment the support surface already comprises a first binding partner, and the surface is adapted to selectively immobilise a second binding partner. It will therefore be appreciated that the support surface according to the first embodiment can be considered to be 'unfunctionalised', and the support surface according to the second embodiment can be considered to be 'functionalised' or 'pre-functionalised'.

Preferably the first of the series of reagents comprises the second or complementary binding partner to the first binding partner, and then the subsequent reagents are chosen from, say, washing or rinsing reagents, and as discussed further below.

Preferably the method of the invention further comprises the step of analysing the nucleic acid sequencing assay during and/or after each said contacting or dispensing step. In preferred embodiments, prior to contacting the support surfaces with a subsequent reagent each said support surface is subjected to a washing or rinsing step with a washing reagent. The washing reagent may be any reagent which can substantially wash off any residual solution from the previous contacting step or reduce the amount of any residual solution and the components present in said solution (active agents like, e.g., apyrase or other suitable enzymes which degrade by-products or otherwise reduce the concentration of by-products).

Whilst the washing reagent may be any reagent which can substantially wash off any residual solution from the previous contacting/dispensing step or reduce the amount of any residual solution and the components present in said solution, and may be an active agent like apyrase, in other embodiments preferably the washing step for removal of excess nucleotide is free from apyrase, as detailed in Mashayekhi F., and Ronaghi M., *Analysis of read-length limiting factors in pyrosequencing chemistry*, Anal. Biochem. (2007), 363(2):

275-287, which is incorporated in its entirely herein by reference. As detailed in Mashayekhi et al, replacing the washing step with an apyrase-free washing step her been shown to improving the read-length of pyrosequencing.

Preferably the rotatable platform is rotated at low speed whilst dispensing the reagents, for example at between about 10 to 200 rpm, so as not to remove reagents added to the target site; and the platform is rotated at high speed whilst dispensing the reagents, for example at between about 400 to 2000 rpm. However, it will be appreciated that other rotational speeds are possible.

In preferred embodiments, each said support surface is prepared for each said subsequent reagent by substantially 'drying' said support surface by rotation of said platform to centrifugally remove any residual reagents such that there is a substantially reduced, preferably substantially no contamination of said support surface with the reagent from the previous step.

According to another aspect the present invention provides use of the platform and support surface combination for conducting an assay. According to a further aspect the present invention provides a kit comprising the platform as discussed herein and one or more support surfaces and optionally one or more reagents for said assay.

Preferably the apparatus for rotating the platform is a motor, and the predetermined rotational speeds are user-selectable and between about 10 to 5000 rpm. The apparatus is also preferably provided with a vacuum extraction system to extract the waste reagents which are spun off the rotatable platform.

The present invention will now be explained in the context of pyrosequencing, however it will be appreciated that the invention is not limited to this assay.

Pyrosequencing

Preferably the nucleic acid sequencing method employed is pyrosequencing. However, it will be appreciated that other methods of sequencing a nucleic acid strand may be utilised, as discussed further below.

Preferably said nucleic acid strand is DNA or RNA or a modified form(s) thereof e.g. following bisulfite treatment or covering additional bases which are not present in naturally occurring nucleic acids. It will be appreciated that copies of the nucleic acid strand are retained on each of the one or more discrete areas.

Preferably the rotatable platform is substantially circular and has a diameter between about 50 to 500 mm. Preferably the rotatable platform comprises between about 2 to 500 wells which are equidistantly spaced from the centre of the rotatable platform. It will be appreciated that the diameter may be any diameter, and the diameter may be chosen to accommodate the number of wells, which may be 1 or more in number. In preferred embodiments the wells are distributed or positioned substantially evenly around the periphery of the rotatable platform to form a substantially circular array.

Preferably the wells contain support surfaces, which are in the form of beads, which are preferably magnetic beads which are adapted to selectively bind, capture, or immobilise a nucleic acid strand (e.g. the sequencing template or the sequencing primer). For example in some preferred embodiments the nucleic acid strand is biotinylated and the discrete areas comprise avidin, and preferably streptavidin or an analogue, for binding the biotinylated nucleic acid strand. Alternatively, the support surfaces or the beads are adapted to bind, capture, or immobilise avidin, and preferably streptavidin, and in a subsequent step the biotinylated nucleic acid strand is selectively immobilised to the avidin/streptavidin bound to the support surfaces. However, it will be appreciated that other chemistries are available for immobilising a nucleic acid strand to a discrete areas. The present invention is not limited to the chemistry which can be employed to immobilise the nucleic acid strand to the discrete areas. In other embodiments, template binding agents could be by way of ligand binding, universal primer/probe or an antibody.

In one embodiment wells may be shallow wells, which may comprise a volume of between about 0.5 to 100 µL. It will be appreciated that the shallow wells may be any shape, and that the wells may be any volume. In some embodiments the wells are about 1 to 5 mm in diameter. However, it will be appreciated that the wells could be any diameter or shape when.

Preferably the rotatable platform is conveniently formed of a plastics material, however, it will be appreciated by the skilled person that other materials are possible, such as glass or quartz. Preferably the plastics material is selected from the group consisting of polycarbonate, polystyrene, or polypropylene. It is also contemplated that the rotatable platform could also be a laminated structure. Whatever the material which the rotatable platform is formed from the platform must be capable of withstanding rotation without deformation, and potentially withstand thermal effects for denaturing the nucleic acid, as discussed further below.

In some preferred embodiments the rotatable platform, which may be a substantially circular disc, further comprises a trough disposed at the periphery of the platform for receiving waste fluids which are spun off or centrifuged away from the surface of the rotatable platform during its rotation. It will be appreciated that once each step or number of steps of the pyrosequencing reaction is completed the unused or waste reagent in the wells should be removed to achieve long read lengths. Creation of centrifugal force by rotation of the rotatable platform causes the waste fluids to be spun off the platform, and in order to improve the handling of the waste fluids a trough is provided. Alternatively wastes reagents could be spun off the platform every, say, 20, 30, 40 or 50 cycles of nucleotide addition, or just before the reagents become sufficiently diluted so as to inhibit the reaction.

In this embodiment it will be appreciated that the total mass of the rotatable platform will increase as additional pyrosequencing reagents are added to the wells and then spun off the platform after each pyrosequencing reaction is complete. Therefore, in an alternative embodiment, it may be desirable that the rotatable platform not include a trough and the housing within which the rotatable platform is positioned be configured to have a trough disposed adjacent the periphery of the platform, such that waste fluids which are spun off the surface of the rotatable platform during its rotation are caught in this 'stationary' trough.

The skilled person, familiar with the techniques and chemistry behind pyrosequencing, will appreciate that the nucleic acid strand immobilised to the support surfaces may need to be denatured to remove the complementary nucleic acid strand. Denaturing may be achieved by any method, however preferred examples comprise heating the wells and the support surfaces or even the entire rotatable platform to a temperature sufficient to denature, e.g. 94 to 99° C., or by exposing the support surfaces to a solvent heated to in excess of 94° C., such as a buffer.

Alternatively, the support surfaces may be exposed to a denaturing composition (e.g. compositions comprising NaOH). Other methods include heating by infra-red or equivalent radiation. It will be appreciated that the rotatable platform should be formed of materials which are capable of withstanding such denaturing conditions.

The rotatable platform could also be enabled to heat and cool so as to hybridise or melt DNA to the captured nucleic acid target or to the captured sequencing primer. In the case of pyrosequencing, once the dsDNA target has been captured and denatured, a sequencing primer is added to hybridise to the ssDNA or, alternatively, the ssDNA is hybridized to the captured sequencing primer. In this case the rotatable platform may be heated to remove any tertiary structures in the ssDNA and then cooled to hybridise the sequencing primer to the immobilised target.

It will be appreciated that heating the chamber may add somewhat to the complexity of the device, since when relatively small volumes of reagents are used the chamber is sealed by suitable means. Alternatively, one may use an oil overlay to reduce evaporation during the heating phase. Other suitable means are well known to the artisan. Alternatively, denaturation reagent could be added to the captured ssDNA and sequencing primer, then buffer of a lower pH added to reduce the pH and anneal the sequencing primer to the DNA target. Once annealed, the pH buffer may be spun off to waste.

The skilled person will appreciate the many advantages which the present invention, in various embodiments, is capable of providing. For example, the present invention enables an increased base read length compared to prior art devices and methods. To explain, prior art methods conduct pyrosequencing in a 0.2 mL microcentrifuge tube (or similar) and reagents are added to the tube sequentially to detect the sequence of the DNA present in the tube. The nucleotides are added sequentially to the reaction containing the DNA in reaction buffer, all enzymes and the substrate(s). The reaction is performed in a 96 or 24 well plate. The plates are heated (28° C.) and shaken during the reaction. Hence, the volume of nucleotides added is more or less equivalent to the volume which evaporates which does not result in a dilution of the reaction mixture but in an accumulation of byproducts. The prior art methods suffer from the drawback that the read lengths are comparatively short which is most likely based on the accumulation of degradation products, e.g. generated by the activity of the apyrase. The present invention does not offer the drawbacks known from the state of the art, since the immobilised nucleic acid strand is contacted with a nucleotide, the remaining nucleotides as well as all reaction products and by-products are subsequently substantially removed from the wells as described above, the support surface is also optionally washed before being contacted with a subsequent nucleotide reagent. It is contemplated that base read length of in excess of 300 or 400 bases are possible, and with improvements to chemistry potentially in excess of 1000 bases.

Further advantages will be evident to the skilled person; however for clarity the invention provides relatively simpler apparatus than prior art flow-through cells. Even further advantages relate to potentially relatively faster sequencing than prior art methods and devices, and that potentially lower volumes of reagents required compared to the prior art. A further limitation of some prior art methods, and in particular the method of conducting pyrosequencing, is the very long time needed for one reaction cycle, i.e. the addition of one nucleotide. In some cases, the time needed for one reaction cycle is normally about 60 seconds or even more which is based on the time needed to degrade all the remaining nucleotides of the previous reaction cycle. Only after complete degradation of substantially all remaining nucleotides of the previous reaction cycle the next nucleotide is added. It will be appreciated that the apparatus as herein described enables the remaining nucleotides to be removed at a much higher speed (i.e. via centrifugation steps, washing steps). This results in a much shorter cycle time for one base being incorporated.

Without wishing to limit the present invention, it is understood that the cycle time can be reduced to approximately 15 seconds, thereby creating an approximate at least a four-fold decrease in run time. However, it is contemplated that the cycle time can be reduced even further.

The present invention also enables improved fluid handling compared to some prior art devices. It is also possible that the present invention could provide increased sensitivity compared to prior art devices given a high-speed photomultiplier can be used instead of a CCD array.

Pyrosequencing is a method of DNA sequencing based on the 'sequencing by synthesis' principle, which relies on detection of pyrophosphate release on nucleotide incorporation rather than chain termination with dideoxynucleotides. 'Sequencing by synthesis' involves taking a single strand of DNA to be sequenced and then synthesizing its complementary strand enzymatically. The 'sequencing by synthesis' methods are based on detecting the activity of a DNA polymerase (a DNA synthesizing enzyme) by detecting a reaction by-product of the nucleotide addition reaction of the DNA polymerase (DNA+xdNTP→DNA$_{+1}$+PPi or a different by-product depending on x. x can also be ATP). In the pyrosequencing reaction the PPi is quantified using an enzyme cascade which generates light.

1. Sulfurylase: APS+PPi→ATP+SO$_4$
2. Luciferase: Luciferin+ATP→Oxoluciferin+PPi+Light
3. Apyrase: degradation of remaining dNTPs and ATP Furthermore, there are several reactions known in the art which may be used to quantify the byproducts like e.g. the use of PPDK (phosphoenol pyruvate dikinase) which transform PPi+PEP+AMP→Pyruvate+ATP+Pi. Furthermore the byproducts may be detected by e.g. change in pH or other detectable parameter changes. The 'sequencing by synthesis' methods may alternatively be based on detecting the activity of a DNA ligase detecting a reaction by-product of the primer addition reaction of the DNA ligase. Suitable methods are well known to a person skilled in the art.

Essentially, the method allows sequencing of a single strand of DNA by synthesizing the complementary strand along it, one base pair at a time, and detecting which base was actually added at each step. The template DNA or the sequencing primer is immobilized, and solutions of A, C, G, and/or T nucleotides are added and removed after the reaction, sequentially. Light is produced only when the added nucleotide complements the first unpaired base or bases of the template. The sequence of added nucleotides which produce detectable signals, e.g. chemiluminescent signals, allows the determination of the sequence of the template. ssDNA template is hybridized to a sequencing primer or vice-versa and incubated with the enzymes DNA polymerase, and optionally ATP sulfurylase, luciferase and/or apyrase, and—by way of example—with the substrates adenosine 5' phosphosulfate (APS) and luciferin. Other reaction cascades providing a detectable signal are well known to the artisan.

In broad overview, pyrosequencing follows the following general steps:

1. The addition of one of the four deoxynucleotide triphosphates (dNTPs) or suitable derivatives thereof to the nucleic acid strand template. The DNA polymerase incorporates the correct, complementary dNTP or its derivative onto the template, which releases pyrophosphate (PPi) stoichiometrically.
2. ATP sulfurylase quantitatively converts PPi to ATP. This ATP triggers the luciferase-mediated conversion of luciferin to oxyluciferin that generates visible light in amounts that are proportional to the amount of ATP. The light produced in the luciferase-catalyzed reaction is detected and analyzed.

3. Unincorporated nucleotides and ATP are subsequently degraded by apyrase or other suitable enzymes.

Several modifications to the classic pyrosequencing protocol are well known in the art and are well suited to be performed on an apparatus according to the present invention. Since the light produced in every single nucleotide incorporation step is proportional to the amount of nucleotides incorporated, suitable software allows for transformation the generated light information in a specific nucleotide sequence pattern. In classic pyrosequencing, the light pattern is called 'pyrogram'. Furthermore, said software preferably allows for the quantification of incorporation ratios of mixed populations at specific positions.

The present invention contemplates sequencing methods that comprise the steps of immobilising the nucleic acid template or target to be sequenced or the sequencing primer and cycles of step-wise nucleotide additions. Whilst the present invention has been exemplified with respect to pyrosequencing, it will be appreciated that the present invention is also useful for other nucleic acid sequencing chemistries, and in particular such chemistries that benefit from a flow through environment and a solid phase. The present invention can also avoid certain of the steps referred to above, or at least make them more convenient. Pyrosequencing requires that ssDNA template is present. Optionally, the support surface also serves to capture dsDNA and denature said dsDNA to leave ssDNA, for example with an annealed sequencing primer ready for pyrosequencing, thus eliminating the need for a separate isolation step.

Specifically, the person skilled in the art would understand that the term "flowthrough DNA sequencing" includes, for example, a method of immobilizing a nucleic acid template or a sequencing primer, hybridising the primer to the template or vice-versa and perform a primer mediated synthesis in a step-wise manner in the presence of nucleotides wherein the nucleotides include, for example, optionally with a strand extension termination moiety, such as a dideoxy moiety, and optionally a detectable label (e.g. Sanger sequencing). A further nucleic acid sequencing method embodiment comprises the steps of: incorporating a labelled nucleotide into the extending primer strand; identifying the incorporated nucleotide; and removal of the strand extension termination moiety and label so that the extending strand is ready for incorporation of a successive nucleotide.

The person skilled in the art would also understand that the term "flowthrough DNA sequencing" includes, for example, nucleic acid sequencing by ligation. It would be clear that the term "nucleic acid sequencing by ligation" comprises immobilising a nucleic acid template or a sequencing primer, hybridising the primer to the template or vice-versa, followed by successive rounds of DNA ligation of, for example, labelled nucleotides or short labelled probes.

It would also be clear to the person skilled in the art that the present invention contemplates any DNA sequencing method which comprises steps of nucleic acid immobilisation and stepwise nucleotide addition and detection.

The method of the invention may also include an optional washing step or enzymatic treatment may improve the removing of the residual or unreacted reagent.

In one embodiment the sequential contacting or dispensing step comprises either:
  a.) A followed by T followed by G and then followed by C nucleotides, followed by A again, etc; or
  b.) A+T+G+C nucleotides are added as a mixture, and the mixture added again, etc.

In another embodiment each said support area is contacted sequentially with a series of reagents comprising A, T, G and/or C nucleotides. The sequential contacting step may comprise one of the following:
  a.) each nucleotide or its analog is added separately and sequentially in any desired or predetermined order,
  b.) A+T+G+C nucleotides or any predetermined or desired subset of these are added as a mixture, and the mixture added again, etc.

The sequential contacting step a.) is particularly useful for the pyrosequencing methodology, and the sequential contacting step b.) is particularly useful if labelled nucleotides are utilised, such as fluorescently labelled nucleotides where each is labelled with a different dye.

It will be appreciated that the entire method is iterative in that the sequence of nucleotides may be added in any predefined order and/or any predefined combination and the sequence repeated a sufficient number of times as required to sequence the nucleic acid template. For example, A, T, G, and C may be added only at a known mutation site. The advantage of this embodiment is that this procedure speeds up known mutation detection, as fewer base additions are required.

Preferably the method of the invention further comprises the step of analysing the nucleic acid strand during and/or after each said contacting step. The analysis can be any analysis however it will be appreciated that in the context of pyrosequencing the analysis step comprises in each step of said analysis identifying the next base pair in the nucleic acid strand by correlating the output of light with the number of nucleotides which have been incorporated to the nucleic acid strand. All appropriate and suitable technical measures to detect the incorporation of a nucleotide may be taken by the artisan. For example, a suitable detector for detecting the light produced by the reaction is a photomultiplier tube (PMT). It will be appreciated that as the rotatable platform is rotated the samples pass the detector, preferably all the samples pass the detector.

In preferred embodiments, prior to contacting the discrete areas with a subsequent reagent each said support surface is subjected to a washing or rinsing step with a washing reagent. The washing reagent may be any reagent which is suitable to wash off residual solution from the previous contacting step, preferably to wash off substantially all residual solution from the previous contacting step. However, in preferred embodiments the washing reagent is the buffer in which the following reaction step is performed. The washing reagent may also contain washing enhancers, such as—by way of example—apyrase, phosphatase, etc. Suitable washing reagents are well known to the killed artisan.

As discussed above the denaturing step may comprise heating the nucleic acid strand to effect denaturing, or exposing the nucleic acid strand to elevated pH, or exposing the nucleic acid strand to a suitable enzyme or enzyme mixture.

In preferred embodiments the method of the invention comprises the step of wherein after the nucleic acid strand is denatured the complementary strand is removed by a rinsed step with a rinsing reagent.

The apparatus for dispensing said nucleic acid strand, for dispensing A, T, G and/or C nucleotides, and for dispensing washing reagent can be any apparatus, however preferably the apparatus is similar to ink jet-type technology, piezo actuated or driven by air pulses. The apparatus is also preferably provided with a vacuum extraction system to extract the waste reagents which are spun off the rotatable platform. The apparatus is also provided with a suitable detection means to detect light produced by the pyrosequencing reaction. Suitable detectors will be known to the skilled person, for example a photomultiplier which may be mounted above the rotatable platform.

The apparatus for denaturing and optionally removing any complementary nucleic acid strand could comprise apparatus for heating the platform to about 94° C., or further syringe or peristaltic dispensers which dispense heated reagents or other denaturing chemicals.

In an alternative detection methodology, one or more solid state pH meters are mounted under each well of the platform. The platform is therefore re-usable as magnetic beads can be used to support the bound DNA for detection of the sequence, and the wells can be washed as described above between each sequencing cycle. Once the sequencing is complete, the beads can be released by removing the magnet from the underneath of the platform, and the platform can be thoroughly washed and then loaded with new samples for analysis. The applicant contemplates that the platform could also be disposable as the cost of ISFET's (51), if customised to the platform, could be low enough (i.e. like semiconductor chips) to make it viable to dispose of the ISFET sensing platform after use.

The skilled person will appreciate that when a polymerase adds a nucleotide an H+ ion is released, thereby changing the local pH, which for example can be detected by solid state pH meters. By way of example, we refer to US 2010/0151479 to DNA Electronics Ltd, which is incorporated herein by reference and which discloses a sensing apparatus comprising an Ion Sensitive Field Effect Transistor (ISFET) arranged to generate an electrical output signal in response to localised fluctuations of ionic charge at or adjacent the surface of the transistor. In this example, fluctuations of ionic charge are measured rather than absolute values. This approach simplifies the chemistry as natural nucleotides can be added sequentially, and when a pH change is detected the beads are captured the well is washed and a new round of nucleotides are added.

Preferably, when using an ISFET detection system on a re-usable platform magnetic beads will be employed to capture the ssDNA. With a disposable ISFET detection platform the surface of the gate of the ISFET could be coated to capture the ssDNA, or magnetic beads could also be used.

According to a further aspect the present invention provides the use of an ISFET detector with the rotatable platform of the invention and employing discrete removable support surfaces in each well. Preferably the ISFET detection elements form the base of each well.

The skilled addressee will understand that the invention comprises the embodiments and features disclosed herein as well as all combinations and/or permeations of the disclosed embodiments and features.

BRIEF DESCRIPTION OF THE DRAWINGS

Preferred embodiments of the invention will now be described, by way of example only, with reference to the accompanying drawings.

FIG. 15 is another embodiment of the invention, and shows a platform having wells which are configured and arranged such that under rotation the beads spin into a cavity and the waste fluid is driven by centrifugal force through a frit or similar filter (60).

DEFINITIONS

Figure 1:
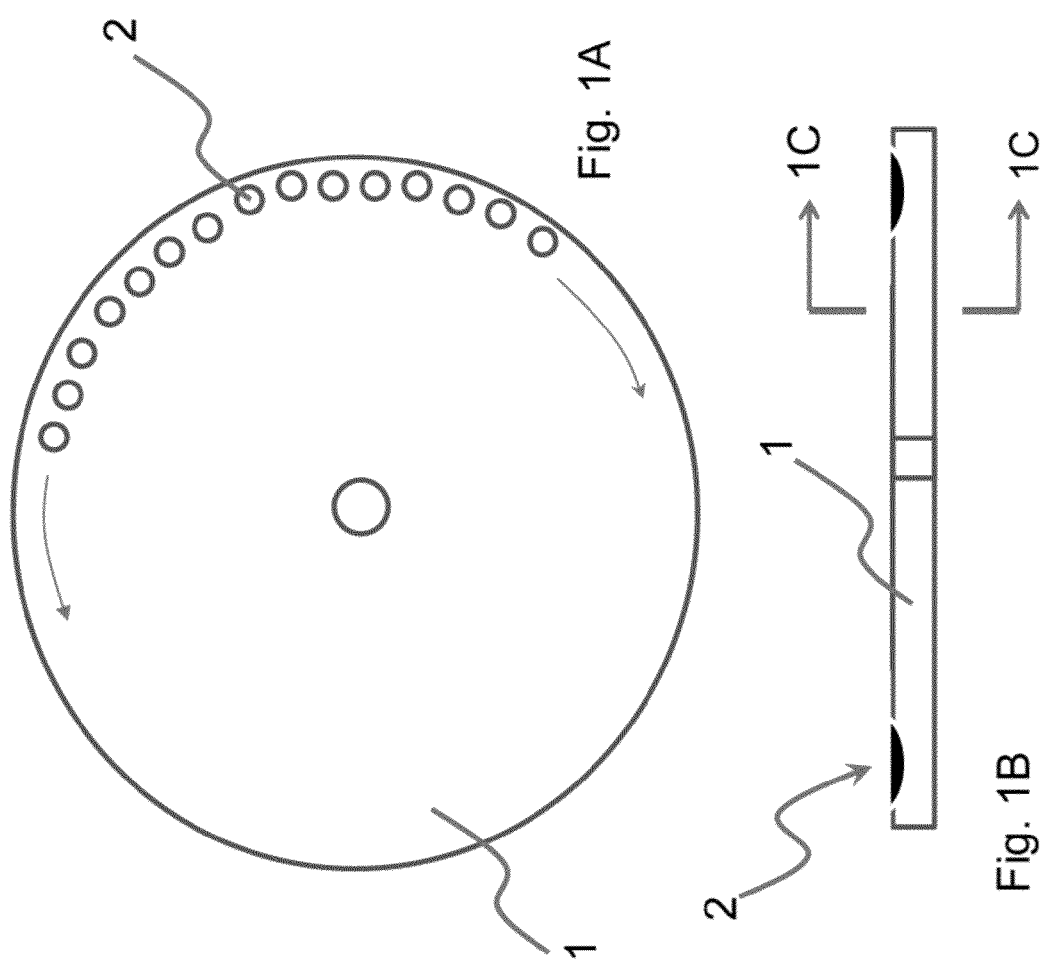
FIG. 1A is a plan view of the rotatable platform of the invention.
FIG. 1B is a side view of the rotatable platform shown in FIG. 1A.
FIG. 1C is sectional view taken on line 1C-1C of FIG. 1B.

In describing and claiming the present invention, the following terminology will be used in accordance with the definitions set out below. It is also to be understood that the terminology used herein is for the purpose of describing particular embodiments of the invention only and is not intended to be limiting. Unless defined otherwise, all technical and scientific terms used herein have the same meaning as commonly understood by one having ordinary skill in the art to which the invention pertains.

Unless the context clearly requires otherwise, throughout the description and the claims, the words 'comprise', 'comprising', and the like are to be construed in an inclusive sense as opposed to an exclusive or exhaustive sense; that is to say, in the sense of 'including, but not limited to'.

In what follows, or where otherwise indicated, '%' will mean 'weight %', 'ratio' will mean 'weight ratio' and 'parts' will mean 'weight parts'.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

To provide a more concise description, some of the quantitative expressions given herein are not qualified with the term 'about'. It is understood that whether the term 'about' is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

The terms 'predominantly' and 'substantially' as used herein shall mean comprising more than 50% by weight, unless otherwise indicated.

The recitation of a numerical range using endpoints includes all numbers subsumed within that range (e.g., 1 to 5 includes 1, 1.5, 2, 2.75, 3, 3.80, 4, 5, etc.).

The terms 'preferred' and 'preferably' refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The enumerated listing of items does not imply that any or all of the items are mutually exclusive. The enumerated listing of items does not imply that any or all of the items are collectively exhaustive of anything, unless expressly specified otherwise. The enumerated listing of items does not imply that the items are ordered in any manner according to the order in which they are enumerated.

As used herein, the term 'binding partner' is understood to mean one of a binding partner pair, which can be any ligand/receptor pair. One of the binding partner pair is referred to as the "first binding partner" and the other of the binding partner pair is referred to as the "second binding partner". For example, the binding partner pairs can be streptavidin/avidin and biotin. The binding partner pairs can, for example, include streptavidin and biotinylated nucleic acid.

As used herein, the term 'rotatable' is intended to mean adapted to be rotated. It should also be understood that the terms 'bead', 'particle' and 'solid support' are used interchangeable, as are 'platform' and 'disc'.

PREFERRED EMBODIMENT OF THE INVENTION

Numerous embodiments are described in this patent application, and are presented for illustrative purposes only. The described embodiments are not intended to be limiting in any sense. The invention is widely applicable to numerous embodiments, as is readily apparent from the disclosure herein. These embodiments are described in sufficient detail to enable those skilled in the art to practice the invention, and it is to be understood that other embodiments may be utilized and that other changes may be made without departing from the scope of the present invention. Accordingly, those skilled in the art will recognize that the present invention may be practiced with various modifications and alterations. References will now be made to the drawings wherein like reference numerals refer to like parts throughout.

A preferred embodiment of the present invention will now be described with reference to pyrosequencing. Description of a preferred embodiment with reference to pyrosequencing should not be taken as limiting the invention to pyrosequencing assays.

Referring to FIG. 1, a rotatable platform (or disc) in the form of a polycarbonate disc 1 is provided which comprises two or more wells 2 adapted to contain at least one support surface in the form of a bead for selectively retaining a nucleic acid strand for conducting sequencing of the nucleic acid. The wells 2 are preferably about 2-3 mm in diameter and are positioned around the circumference of the disc 1 in equally spaced intervals. For example, a disc 1 having a diameter of 120 mm has a circumference of 377 mm, and by forming 3 mm diameter discrete areas 2 spaced apart by 6 mm (between centres of discrete areas/target sites 2) at radius of 55 mm from the centre of the disc 1 results in approximately 57 wells around the periphery of the disc 1. However, the number of wells could be a smaller or greater number by using either a larger disc 1 or smaller discrete areas, e.g. 0.5 mm diameter with a spacing of, say, 1 mm, or any combination thereof. Preferably the wells 2 are shallow wells, which comprise a volume of between about 0.5 to 100 μL.

Figure 2:
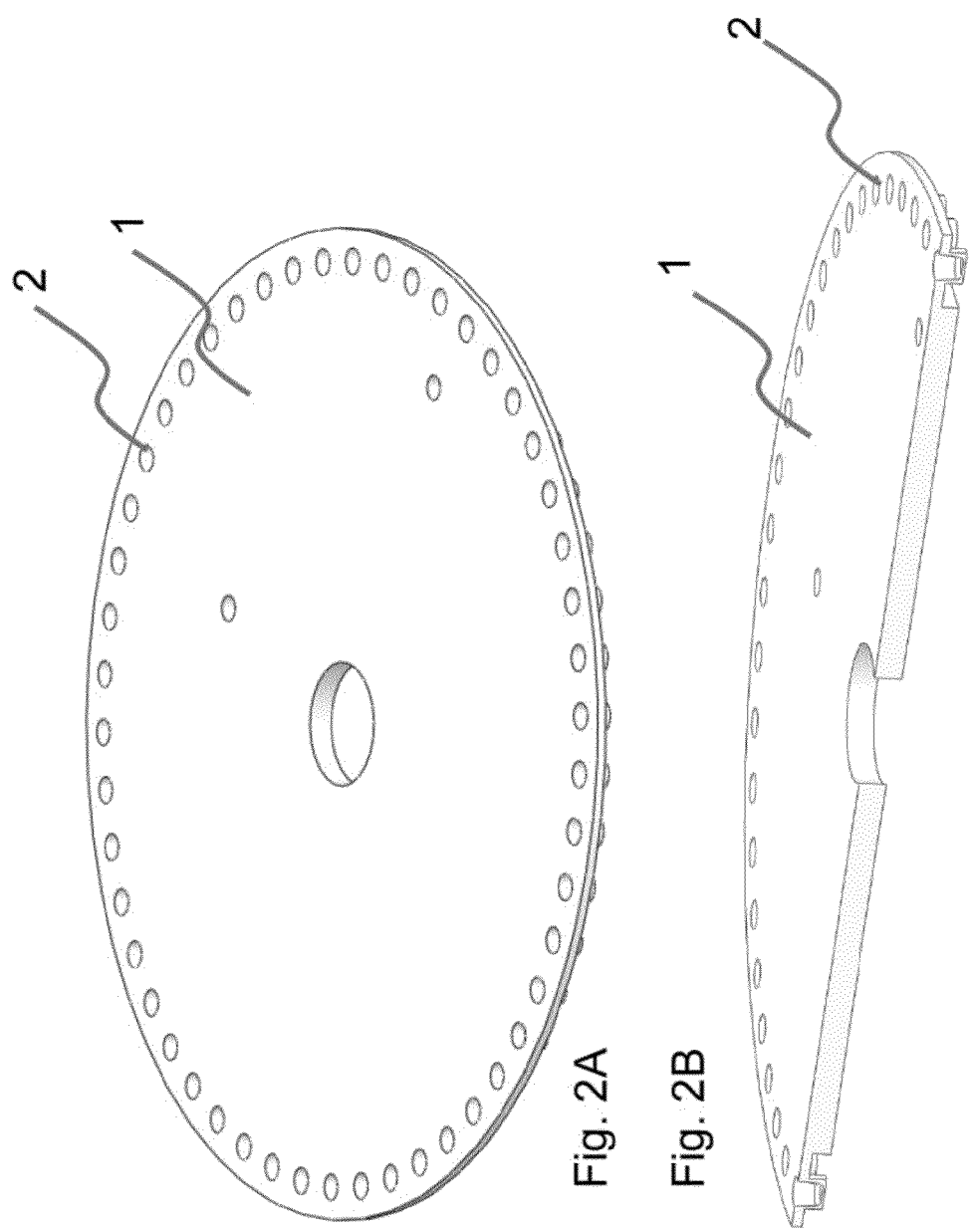
FIG. 2A is a perspective view and FIG. 2B is a cut-away perspective view of an embodiment of the rotatable platform shown in FIG. 1.

Another embodiment can be seen in FIG. 2, in which like features have been given like reference numerals. In this example, the rotatable platforms are 120 mm in diameter with 50 wells equally spaced around the periphery. The wells are about 3 mm in diameter, and can be fabricated from materials including polycarbonate, clear polystyrene and white high impact polystyrene (HIPS). Platform thicknesses are typically 1 mm to 5 mm, and well depths of about 4 mm.

The sequencing method preferably employed is pyrosequencing. However, it will be appreciated that other methods of sequencing a nucleic acid strand may be utilised, as discussed previously. Preferably the wells 2 contain support surfaces adapted to selectively immobilise the nucleic acid strand. For example, the nucleic acid strand may be biotinylated and the support surfaces comprise streptavidin for binding the biotinylated nucleic acid strand thereto. However, it will be appreciated that other chemistries are available for immobilising a nucleic acid strand to the support surfaces.

According to a method of the invention for conducting sequencing of a nucleic acid strand, a rotatable platform 1 is provided and the nucleic acid strand is immobilised to support surfaces which are contained in wells 2. Any complementary nucleic acid strand is then denatured and removed, for example by heating the platform 1 and therefore the support surfaces to about/approximately 94° C. The support surfaces is then contacted sequentially with A, T, G and C nucleotides by dispensing a suitable reagent into the well 2, wherein between each contacting step the platform 1 is rotated such that any residual or unreacted nucleotide is substantially centrifugally removed from the well 2.

The method of the invention further comprises the step of analysing the nucleic acid strand during and/or after each said contacting step. The analysis step comprises detecting the next base pair in the nucleic acid strand by correlating the output of light resulting from the incorporation of nucleotide with the number of nucleotides which have become bound to the nucleic acid strand. A suitable detector for detecting the light produced by the reaction is a photomultiplier. It will be appreciated that as the rotatable platform 1 is rotated all the samples pass the detector. If no nucleotide is incorporated then there is no light signal and the reaction mixture is spun off (either every cycle or every 10-50th cycle (say) but less than the 80th cycle) using centrifugal force, and another round is commenced with the next nucleotide.

In preferred embodiments, prior to contacting the well 2 with a subsequent nucleotide each support surface 2 is subjected to a washing or rinsing step with a washing reagent. The washing reagent may be any reagent which can substantially wash off any residual solution from the previous contacting step, and is preferably a PCR buffer.

Preferably the rotatable platform 1 is rotated at low speed whilst dispensing the nucleotide reagents and enzyme, for example at between about 10 to 200 rpm, and the platform 1 is rotated at high speed whilst dispensing the washing reagent, for example at between about 400 to 4000 rpm.

Figure 3:
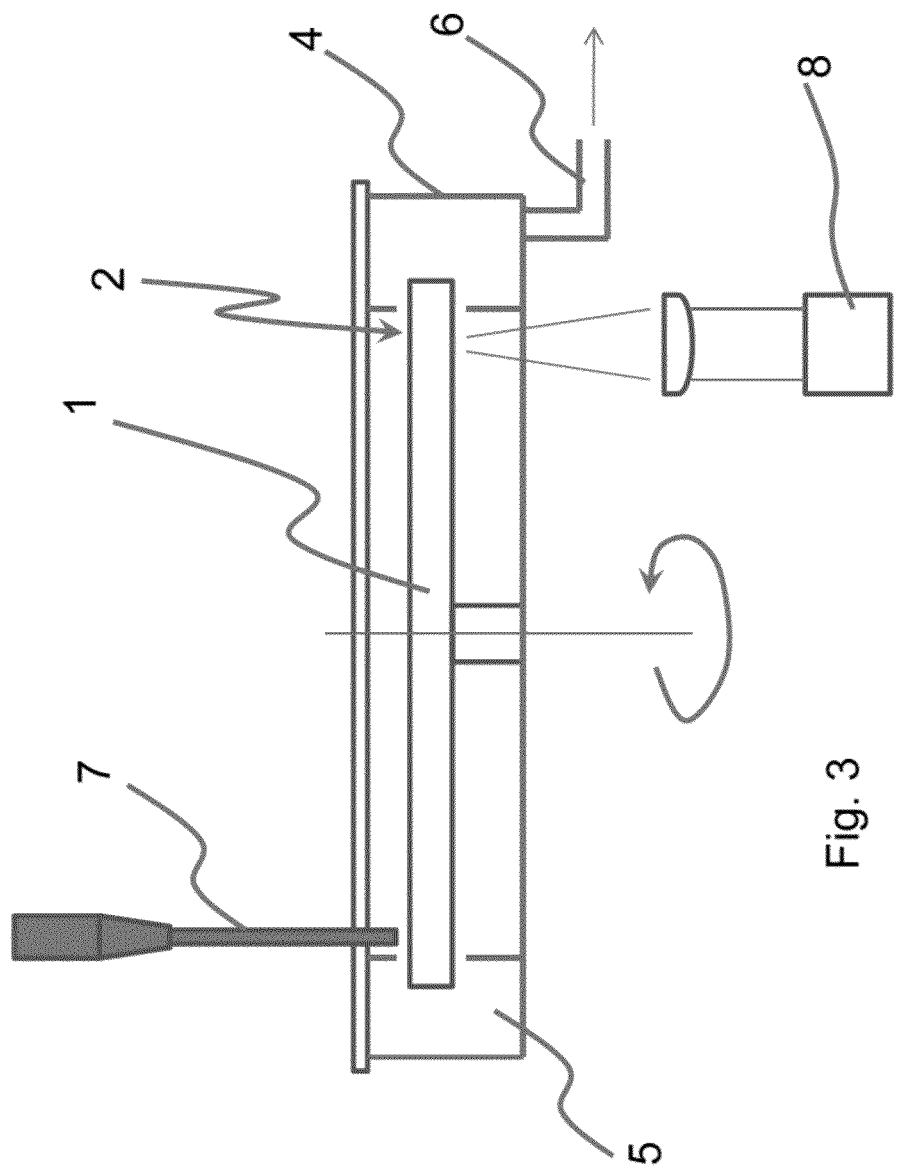
FIG. 3 is a sectional view of apparatus having the rotatable platform shown in FIG. 1A installed therein.

Referring to FIG. 3, the present invention also provides apparatus for use with the rotatable platform 1 for sequencing a nucleic acid strand. The apparatus comprises a motor 50 for rotating the platform 1 at a predetermined controllable user-selectable rotational speed, such as a motor capable of delivering rotational speeds of between about 10 to 4000 rpm. Apparatus is also provided for dispensing the nucleic acid strand into the wells 2 for immobilising the nucleic acid strand to the support surfaces. Such apparatus may take the form of ink jet-type technology or a suitable dispenser 7 such as a syringe pump. Apparatus is also provided for dispensing A, T, G and C nucleotides into contact with the support surfaces and for dispensing a washing reagent. Again, such apparatus may take the form of ink jet-type technology. Apparatus is also provided for denaturing and removing any complementary nucleic acid strand, and such apparatus may take the form of a heating coil (not shown in this Figure) disposed within the housing 4.

Figure 4:
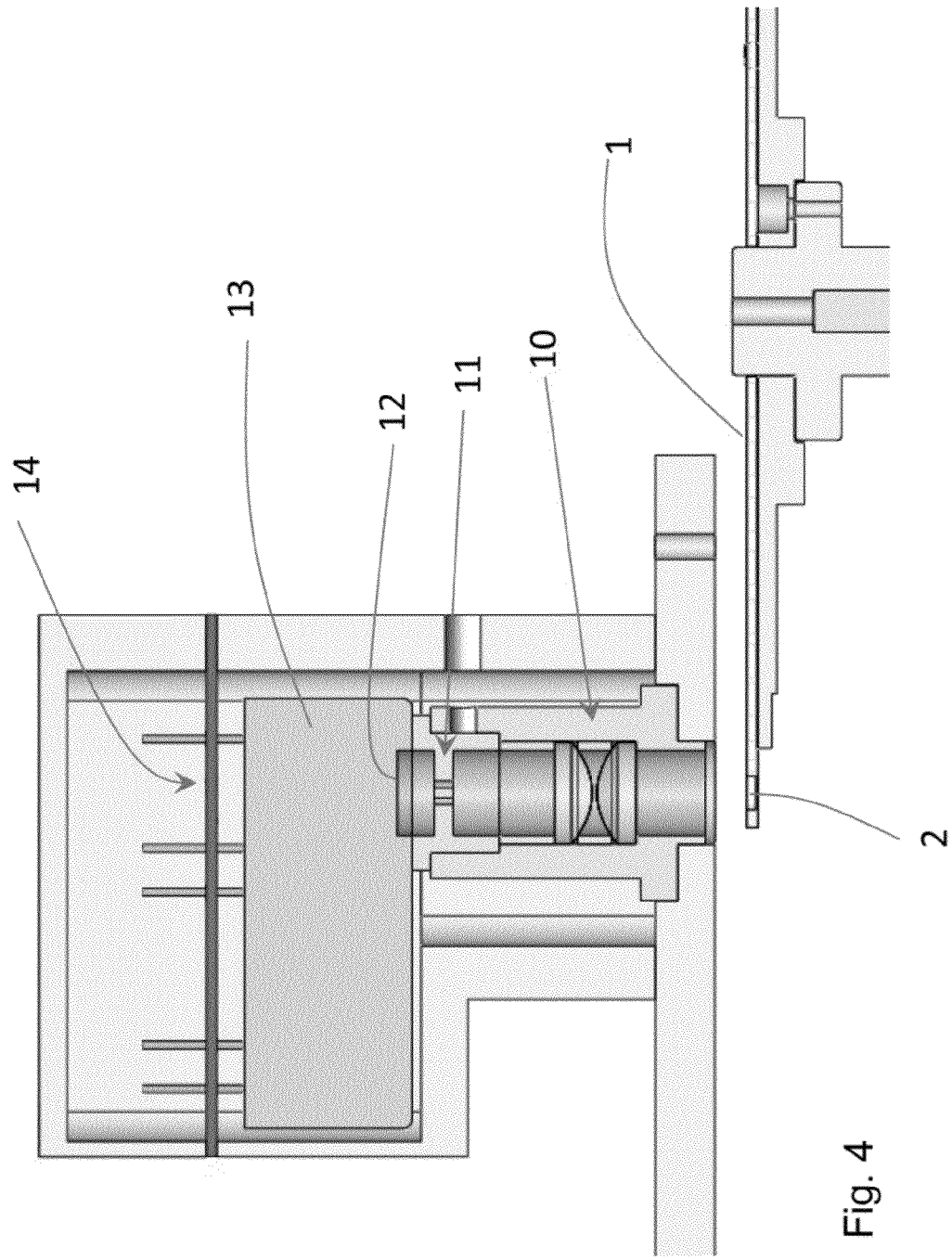
FIG. 4 shows optical detection apparatus utilising focussing optics for monitoring a reaction.
Figure 5:
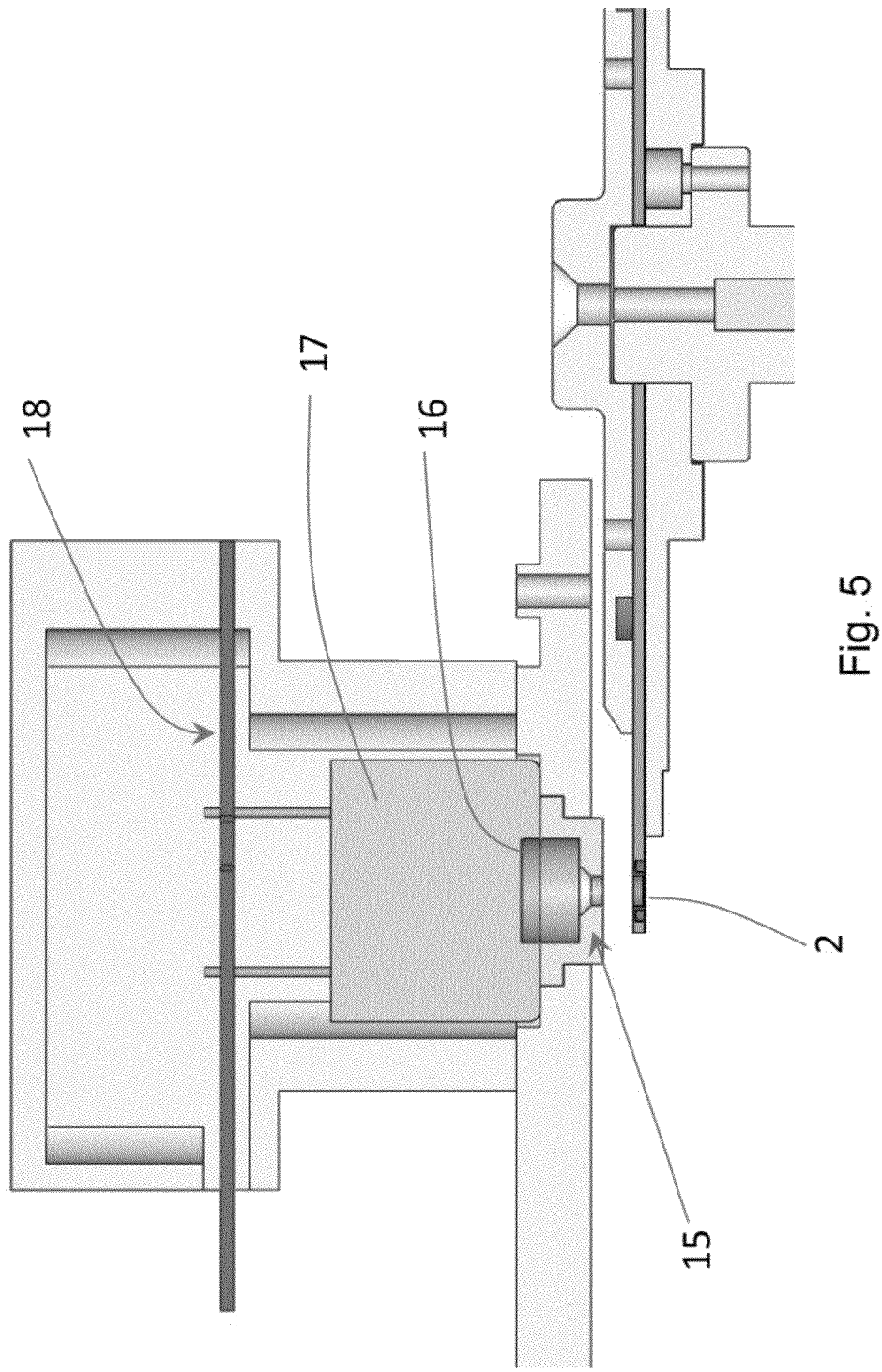
FIG. 5 shows optical detection apparatus utilising direct imaging for monitoring a reaction.

A suitable detector 8 is also provided to detect light produced by the pyrosequencing reaction. Suitable detectors will be known to the skilled person, for example a photomultiplier which may be mounted above the rotatable platform 1. Particular reference is now made to FIGS. 4 and 5 which show various embodiments of photomultiplier detectors for use in the invention. One optical configuration uses focusing optics (FIG. 4) and the second uses direct imaging (FIG. 5). FIG. 4 details a focussing lens 10, an aperture 11, a photosensitive surface 12, a photomultiplier 13 and detection electronics 14. FIG. 5 details an aperture 15, a photosensitive surface 16, a photomultiplier detector 17 and detection electronics 18.

The rotatable platform 1 can be rotated a low speed to dispense the enzyme and nucleotide(s) mixture (i.e. 200 rpm or less) where the centrifugal force is low enough not to move the mixture from the wells 2 and to allow for the reaction to proceed and optical detection to be completed. Wash reagents can be added at high rotor speed, (i.e. 400+ rpm) so the wash removes all reagents from the wells 2 and does not substantially contaminate between wells 2.

EXAMPLES

Pyrosequencing Using Magnetic Beads

The use of pyrosequencing to determine the nucleotide sequence of a DNA target, requires the immobilisation of the DNA target to a solid support. A simple description of the pyrosequencing protocol is as follows:

1) Immobilisation of biotinylated double stranded DNA to a solid support;
2) Separation of non-biotinylated strand through chemical denaturation;
3) Removal of non-biotinylated strand through washing;
4) Annealing of oligonucleotide primer to facilitate the start of the sequencing process;
5) Addition of enzyme and substrate mixes to enable pyrosequencing;
6) Dispensation of the first deoxyribonucleotide (dNTP), which is incorporated in to the target DNA by the DNA polymerase (ensuring both nucleotides are complementary);
7) Upon incorporation of the complementary base a molecule of pyrophosphate is released, which is converted into a light signal through a cascade of enzymatic reactions. The intensity of the signal is used to determine if one or more nucleotides are present in a row;
8) Excess dNTP not incorporated are degraded to ensure they are not incorporated during the next part of the sequencing reaction. This ensures that the sequence remains in synchronization between all target templates;
9) Continue the sequencing reaction by adding the next complementary base.

The immobilisation of biotinylated DNA, which is used in the pyrosequencing reaction, can be achieved using magnetic bead particles 55 coated with streptavidin or neutravidin. Magnetic particles 55 offer greater surface area and allow for mobility within the reaction solution, increasing the binding capacity and probability of locating the biotinylated DNA target.

In this example, immobilisation of DNA template was achieved by mixing the magnetic bead particles 55 with the biotinylated DNA target along with a binding buffer into the well 2 of a platform/disc 1 for a set period of time (e.g. 10 min). Following the immobilisation period, unbound template and supernatant containing various other reagents, which are undesired in the pyrosequencing reaction, were removed through centrifugation. Prior to centrifugation a magnetic ring 20 was raised into contact with the platform, immobilising the magnetic particles to the bottom of the well. The magnetic ring was dropped to less than 1 mm below the platform surface, providing a sufficient magnetic field to retain the magnetic bead particles within the well whilst allowing the platform to spin and centrifuge the supernatant out at speeds greater than 2000 rpm. A wash step using a buffer containing detergent was applied to ensure sufficient removal of the supernatant. The same centrifugal steps were used to remove the wash buffer.

Denaturation of the un-biotinylated DNA strand was achieved using the denaturant sodium hydroxide, which was applied for no more than 20 sec. The denaturant was removed using centrifugation and a wash buffer applied to maximise removal. Again the magnetic ring was applied to allow for centrifugation of the supernatant while retaining the magnetic bead particles within the wells.

To facilitate the pyrosequencing reaction, a sequencing primer was added and hybridised to the DNA target though an annealing process of heating the sample to over 80° C. and cooling to a temperature below 30° C.

On completion of the annealing process, the pyrosequencing enzyme mix was dispensed into the wells along with a substrate mix containing APS and luciferin. The magnetic bead particles were vibrated in the reaction solution to ensure that the reaction occurred randomly. To explain, the platform was vibrated sufficiently so that the beads were agitated and therefore the solution and the bead particles were thoroughly mixed together.

Finally, the sequence was determined by dispensing a small amount of a dNTP into the reaction mix and measuring a light signal if the complementary base existed at that point in the sequence. A period of 1 min was allowed to ensure that excess unbound dNTP was degraded by the apyrase. The sequence was determined by dispensing any one of the dNTP. As the platform is rotated during the reaction it is also vibrated to ensure that the magnetic beads are kept in constant motion and to additionally prevent them from aggregating or clumping together.

Magnetic Bead Particles

Various types of magnetic bead particles were assessed for performance.

Dynabeads MyOne Streptavidin C1 (Invitrogen): superparamagnetic beads of 1 μm diameter with a monolayer of covalently coated streptavidin to the hydrophilic bead surface;

Sera-Mag Magnetic SpeedBeads (Thermo Scientific): 1 μm magnetic carboxylate-modified base particles, made by a core-shell process, covalently coated with neutravidin;

Streptavidin Mag Sepharose (GE Life Sciences): streptavidin coupled to magnetite-containing sepharose beads.

The magnetic bead particles were assessed for:
1) Ability to immobilise biotinylated DNA target;
2) Remain within a well during the centrifugation process;
3) Avoided nonspecific binding of protein during the pyrosequencing reaction Results Immobilisation It was found that all three bead types were capable of immobilising biotinylated DNA. The highest pyrosequencing peak signal heights were observed for the Sera-Mag Magnetic SpeedBeads Neutravidin followed by the Dynabeads MyOne Streptavidin C1 and then the Streptavidin Mag Sepharose (See FIGS. 6A to C). The signal for the Streptavidin Mag Sepharose beads was significantly lower compared with the other two bead types. Two reasons were discovered, first, due to the size and weight of the beads they did not mix as well under standard vibrating conditions; second, the dark colour of the beads attenuated the light signal through absorbance. A solution to the first issue was to vibrate at a greater frequency. Indeed, higher vibrating frequencies allowed for better mixing and therefore signal peak heights (see FIG. 7).

Centrifugation

It was determined that in order to achieve optimum removal of undesired reaction molecules from the immobilised DNA, the rotational speed for centrifugation needed to be above 2000 rpm. Results using DNA isolated from a polymerase chain reaction, with washing centrifugation at 1500 rpm, demonstrated a high peak upon addition of the enzyme and substrate mix (see FIG. 8). The resulting sequencing peaks were significantly attenuated. The cause of the high peak after addition of the enzyme and substrate could be explained by poor removal of the PCR constituents during the wash steps following DNA immobilisation to the magnetic bead particles. The residual dNTP from the PCR would have all incorporated upon addition of the enzyme and substrate mix, completing the sequence instantaneously, thereby delivering a single high peak with a subsequent attenuation of the remaining sequencing reaction due to little remaining non-incorporated template. The data demonstrated that rotational velocities greater than 2000 rpm were required to achieve complete removal of supernatant.

Applying centrifugal velocities greater than 2000 rpm resulted in all but the streptavidin mag sepharose beads from being displaced from the wells. Due to their larger size, these beads remained within the wells at velocities greater than 2000 rpm.

Nonspecific Binding

Due to the composition of the outer shell of some of the beads, nonspecific binding of the enzymes used in the pyrosequencing reaction can have an adverse affect on the resultant peaks and sequence. One characteristic of this phenomenon is the widening of the peaks. This is attributed to a reduction in the enzyme apyrase, which degrades excess unbound nucleotides. Reduced amounts of apyrase will also result in the excess nucleotides incorporating nonsynchronously, causing the sequence to shift out of phase. The resultant sequence thereby becomes incomprehensible as peaks are observed for nucleotide injections that are not expected to have any signal.

Figure 9:
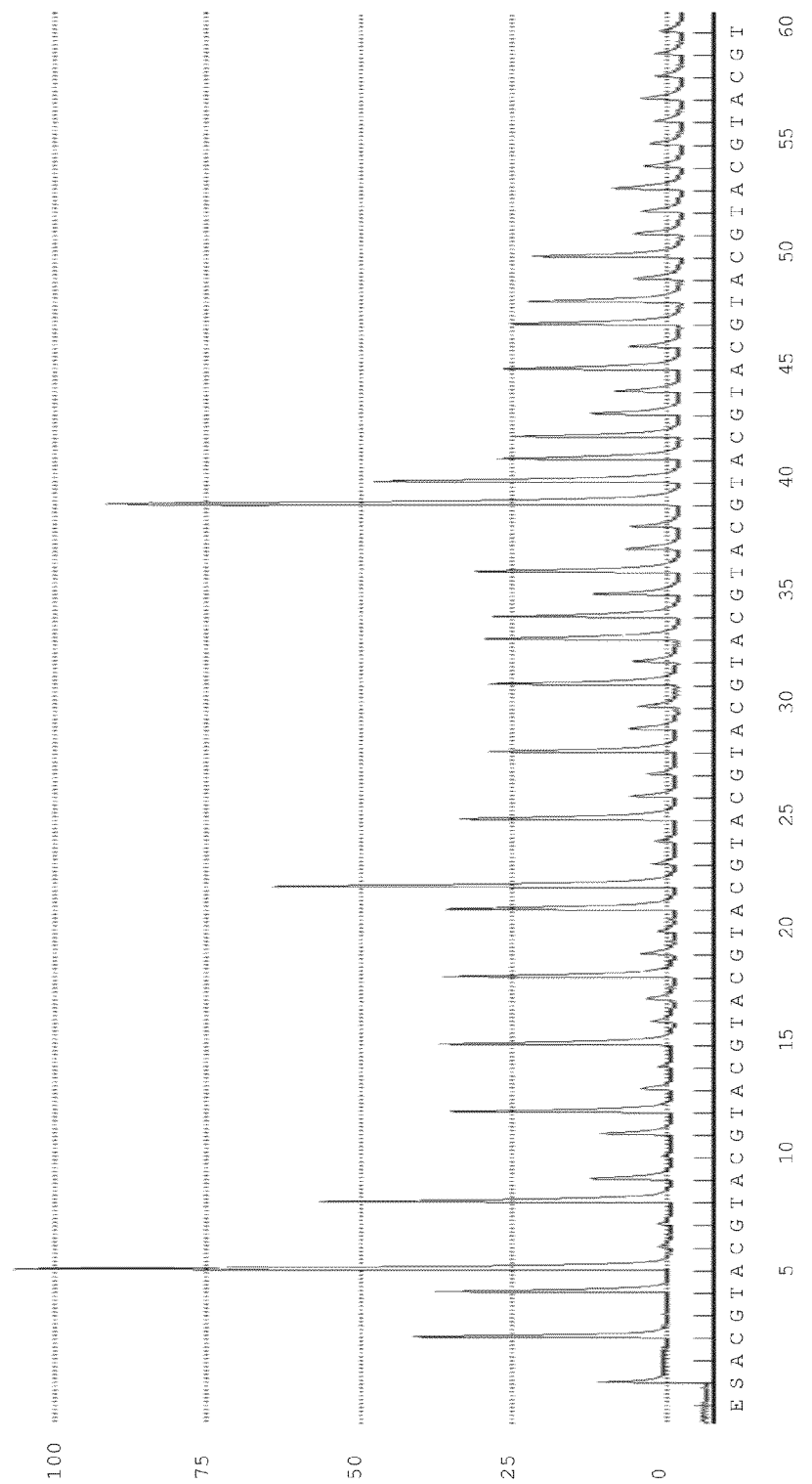
FIG. 9 shows phase shifting and wider peak signals observed during pyrosequencing using DNA target immobilised to Dynabeads MyOne Streptavidin C1 beads (SEQ ID NO:6).

Such issues were observed for the Dynabeads MyOne Streptavidin C1 beads (see FIG. 9). Indeed, both the peak widths and unspecific peak heights were the greatest compared with the other two beads. The least affected bead was the Streptavidin Mag Sepharose bead particles. Without wishing to be bound by theory, it is believed that the sepharose shell is inert, thereby avoiding nonspecific binding. Conversely, the bead surface for the Dynabeads MyOne Streptavidin C1 bead particles contains a charge that attracts the oppositely charged apyrase, thereby binding it to the bead. The bound apyrase can no longer be used to degrade the excess nucleotides, causing a phase shift in the sequence.

CONCLUSION

Based on the observations for the different bead types, it was concluded that the optimum bead to use was the Streptavidin Mag Sepharose beads, however it should be appreciated that the other beads are still viable for the method of the invention. The magnetic particles were capable of immobilising the DNA target with washing centrifugation carried out at certain velocities to ensure cleaner templates for sequencing. The inert out shell also meant that non-specific binding of the pyrosequencing enzymes was not an issue affecting sequencing performance through nonsynchronous incorporation of dNTP.

Figure 6A:
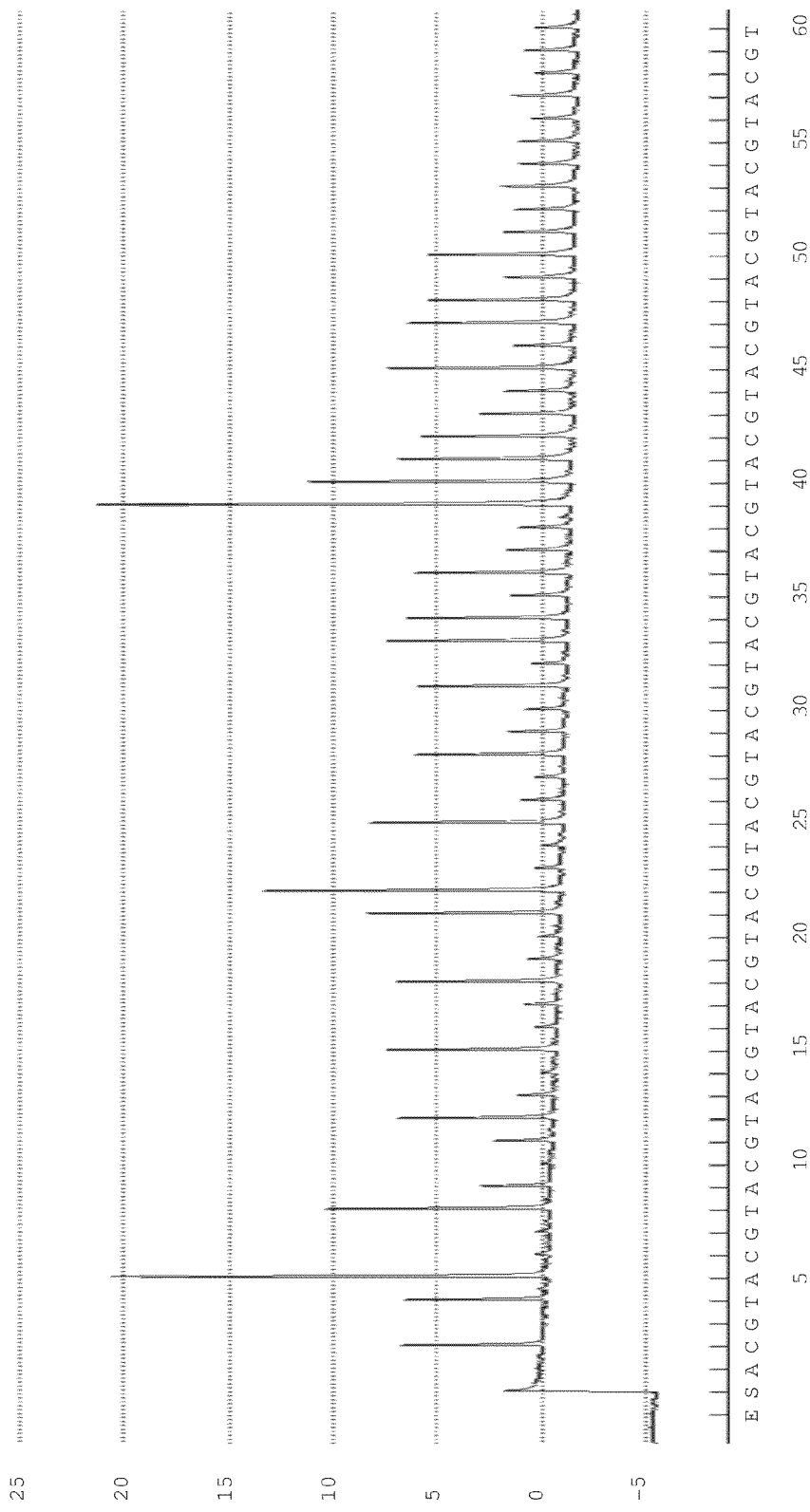
FIGS. 6A to C shows pyrosequencing peak heights for A) Streptavidin Mag Sepharose (SEQ ID NO:1), B) MyOne Streptavidin C1 (SEQ ID NO:2), and C) Sera-Mag Magnetic SpeedBeads Neutravidin (SEQ ID NO:3).
Figure 6B:
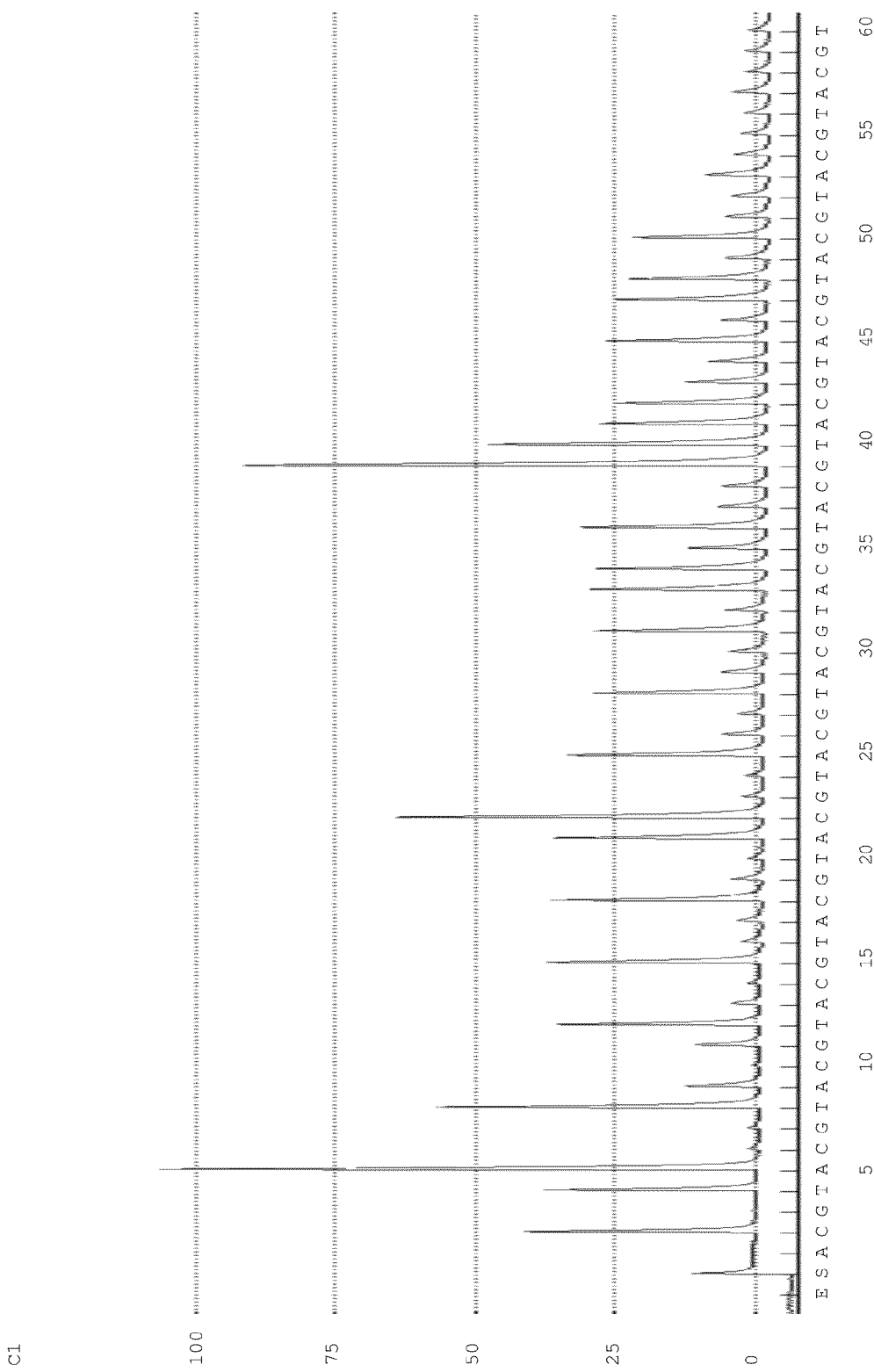
Figure 6C:
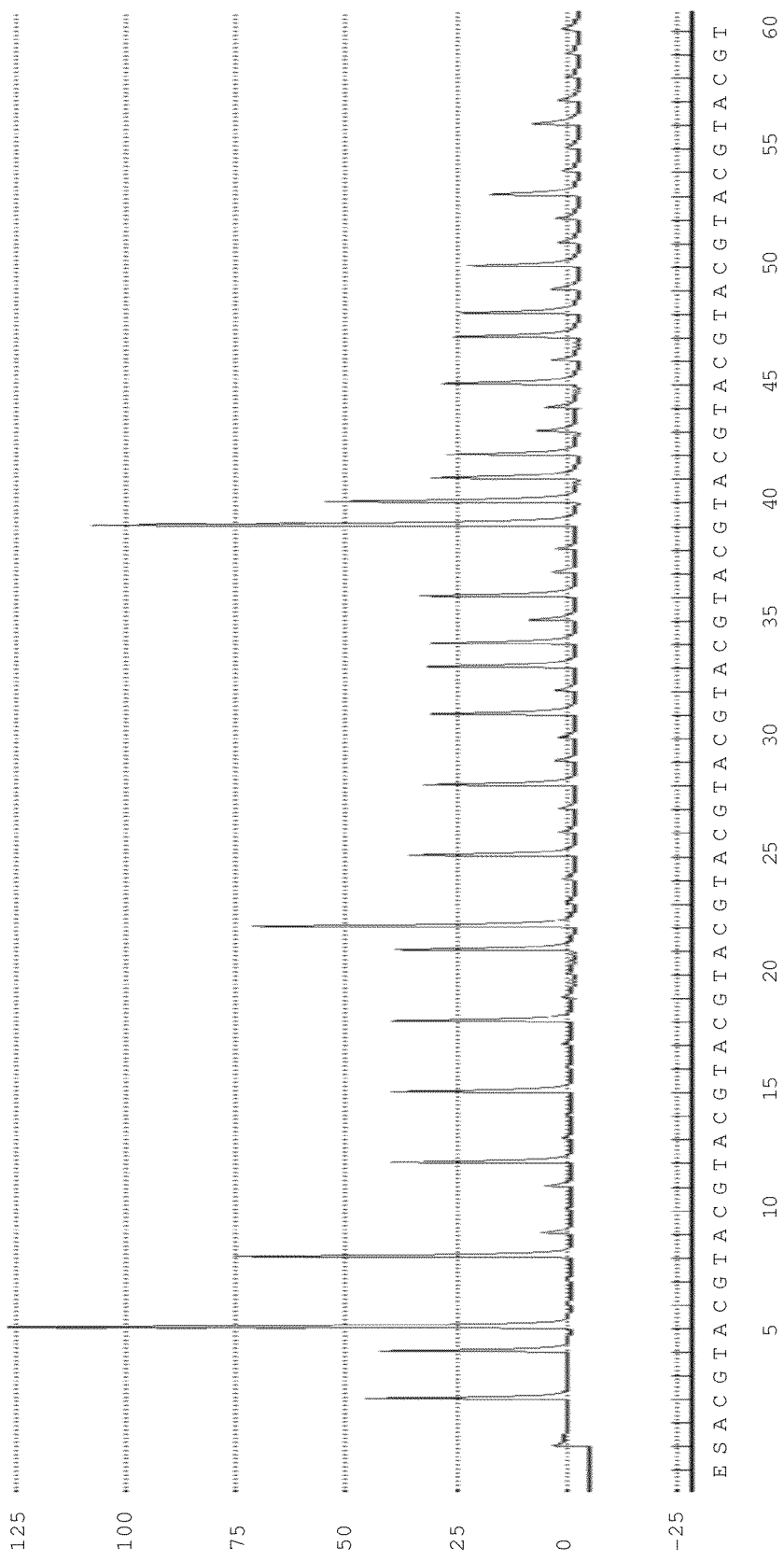

FIGS. 6A to C shows pyrosequencing peak heights for A) Streptavidin Mag Sepharose, B) MyOne Streptavidin C1, and C) Sera-Mag Magnetic SpeedBeads Neutravidin. One picomole of DNA template was added to a solution of 10 µL binding buffer and incubated for 10 min. The immobilised beads were washed in buffer solution prior to and following denaturation with NaOH. Sequencing primer was added at 400 nM concentration and annealed by heating to 80° C. for 60 seconds and then cooled to 30° C. Enzyme and substrate were added and the pyrosequencing reaction conducted de novo using 15 cycles of dATP, dCTP, dGTP and dTTP. The highest peaks were observed for the Sera-Mag Magnetic SpeedBeads Neutravidin.

Figure 7:
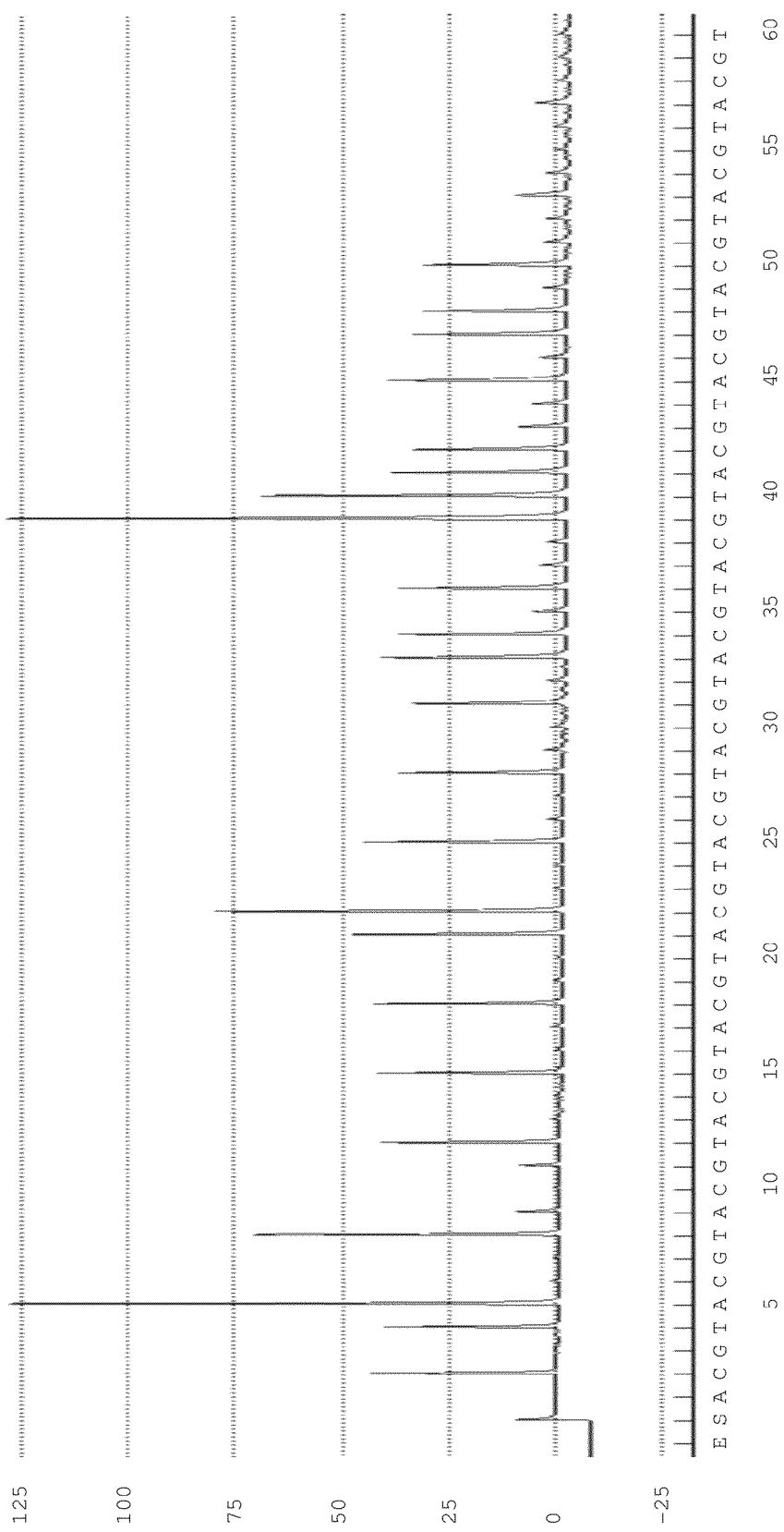
FIG. 7 shows pyrosequencing peaks achieved for the Streptavidin Mag Sepharose beads using a higher frequency of mixing (SEQ ID NO:4).

FIG. 7 shows pyrosequencing peaks achieved for the Streptavidin Mag Sepharose beads using a higher frequency of mixing. Signal peaks increased from an average single peak height of 5 to over 40 units. However, due to the attenuation of signal though the darker colour of the magnetic bead particles, the peak heights did not exceed that observed for the other two beads.

Figure 8:
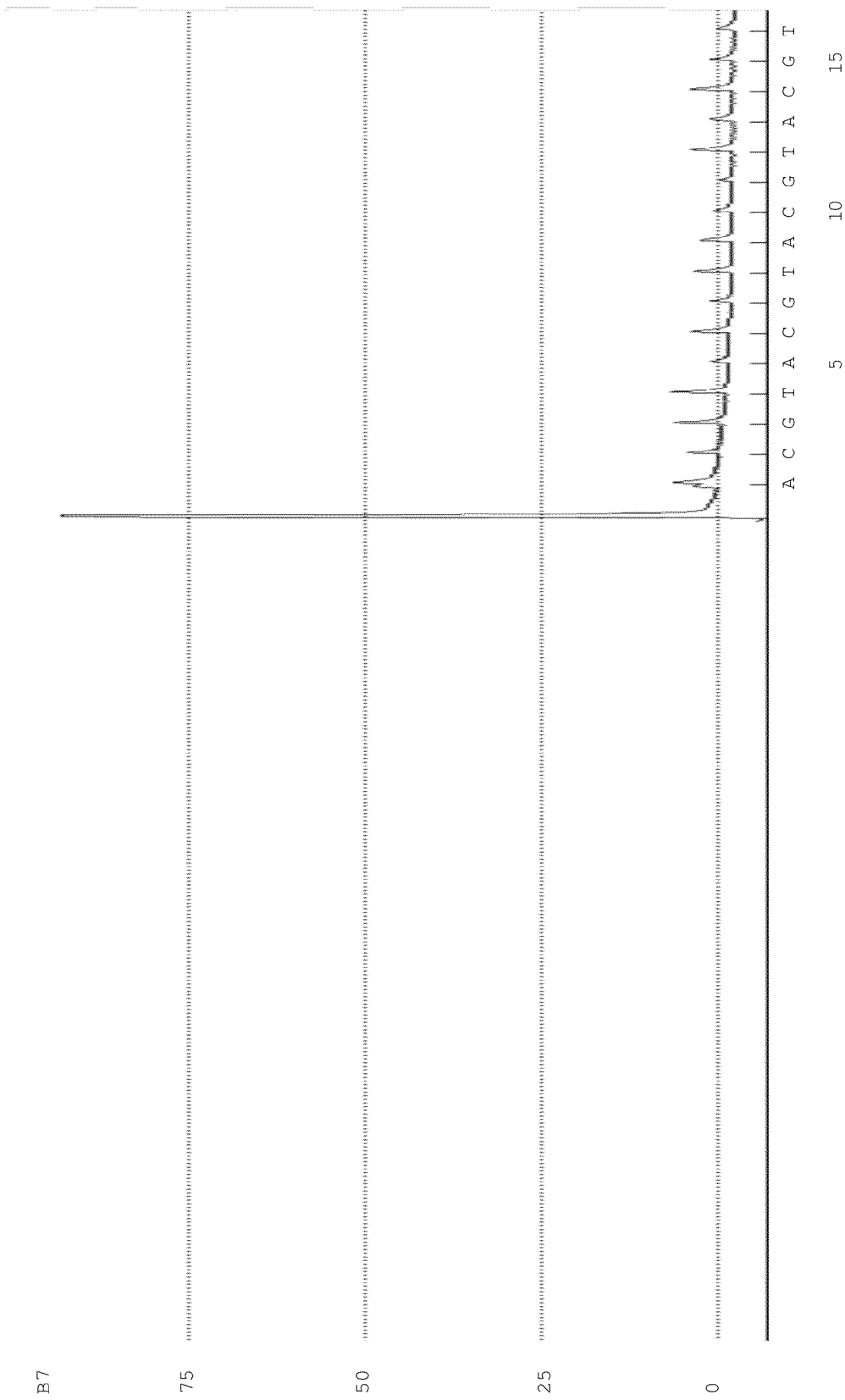
FIG. 8 shows a high peak following addition of enzyme and substrate mixes to a PCR amplicon immobilised to Sera-Mag Magnetic SpeedBeads Neutravidin washed at a centrifugal speed of 1500 rpm (SEQ ID NO:5).

FIG. 8 shows a high peak following addition of enzyme and substrate mixes to a PCR amplicon immobilised to Sera-Mag Magnetic SpeedBeads Neutravidin washed at a centrifugal speed of 1500 rpm. The subsequent sequencing reaction peaks following the addition of the enzyme and substrate mix was significantly attenuated. The same beads did not remain within the well after centrifugation above 2000 rpm.

FIG. 9 shows phase shifting and wider peak signals observed during pyrosequencing using DNA target immobilised to Dynabeads MyOne Streptavidin C1 beads.

Figure 10:
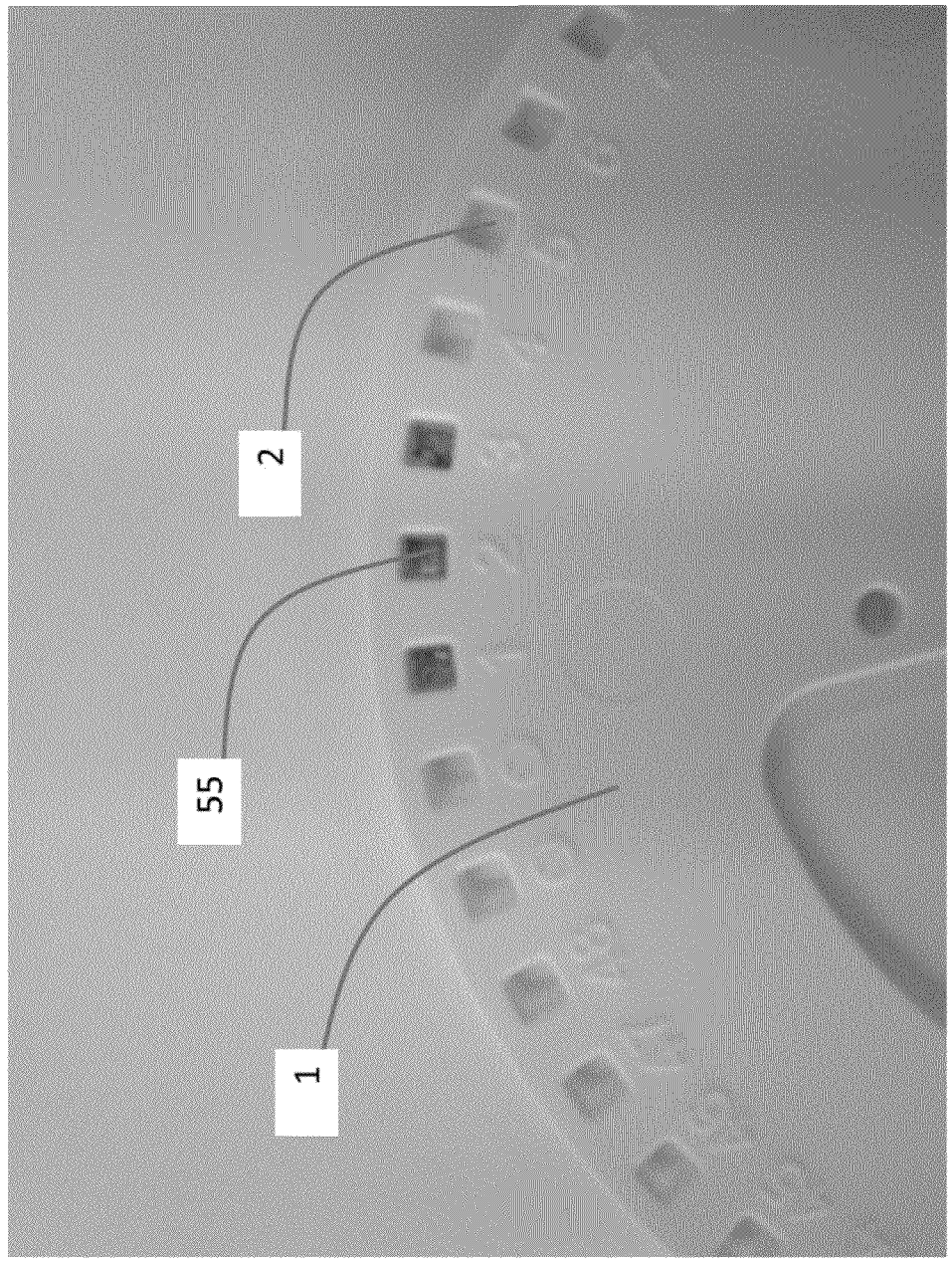
FIG. 10 is a photograph of an actual production platform showing magnetic beads loaded into wells 1 to 3.

FIG. 10 is a photograph of an actual production platform showing magnetic beads loaded into wells 1 to 3.

Figure 11:
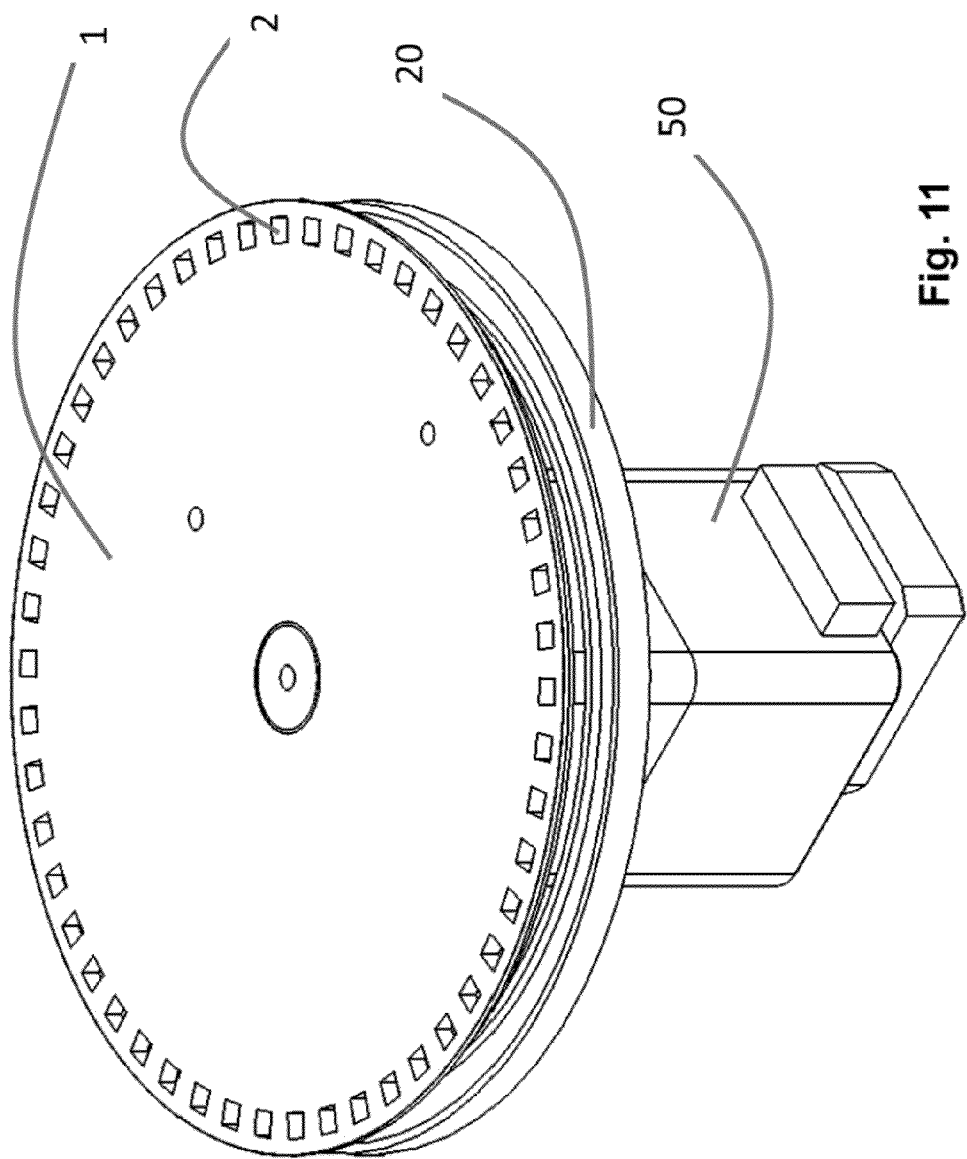
FIGS. 11 and 12 are perspective views of a platform according to the invention engaged with a motor (50) for rotating the platform, and show an annular peripheral magnetic ring (20) in a first position where there is little or no magnetic force being applied on the platform.
Figure 12:
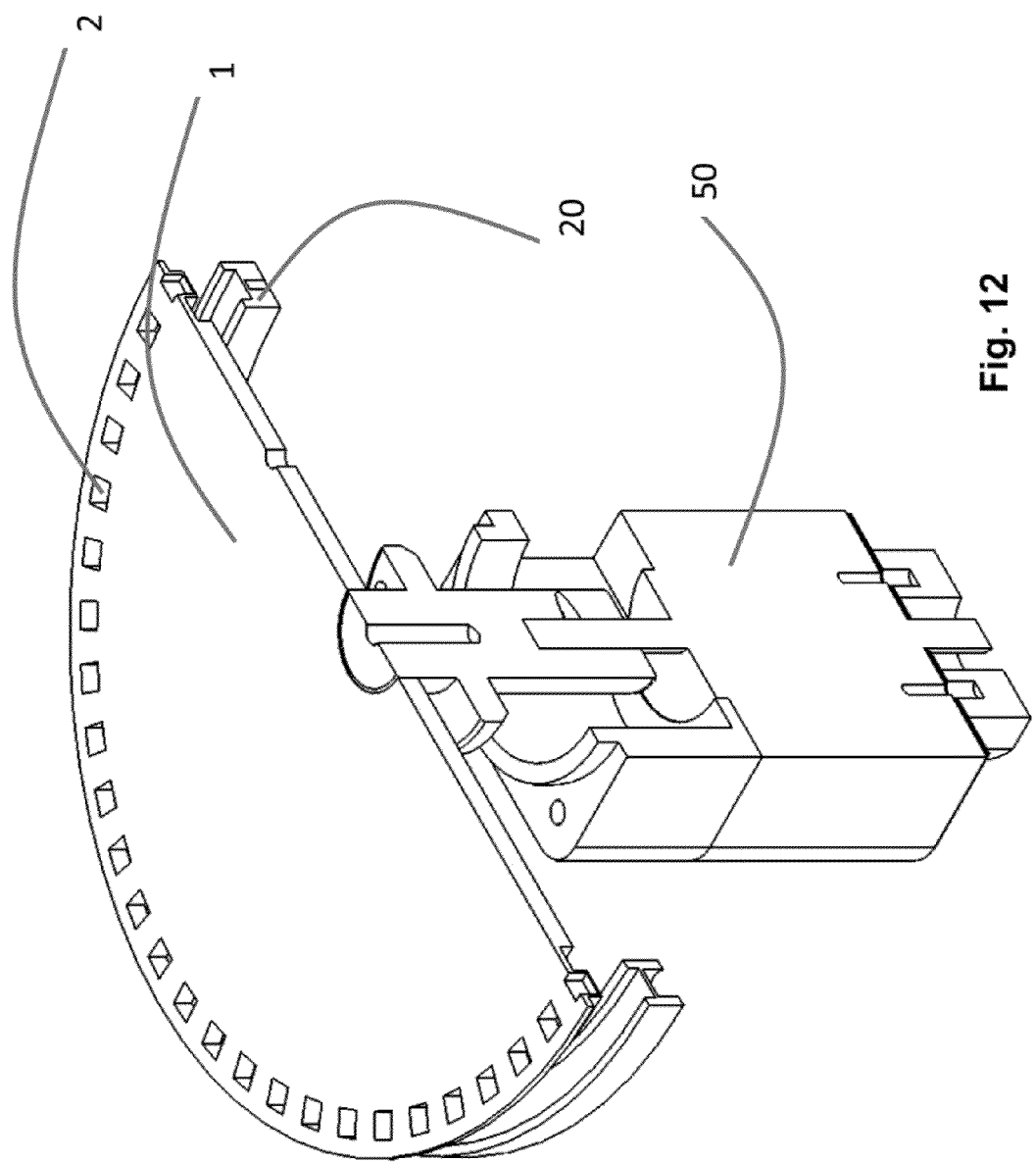

FIGS. 11 and 12 are perspective views of a platform according to the invention engaged with a motor for rotating the platform, and show an annular peripheral magnetic ring in a first position where there is little or no magnetic force being applied on the platform.

Figure 13:
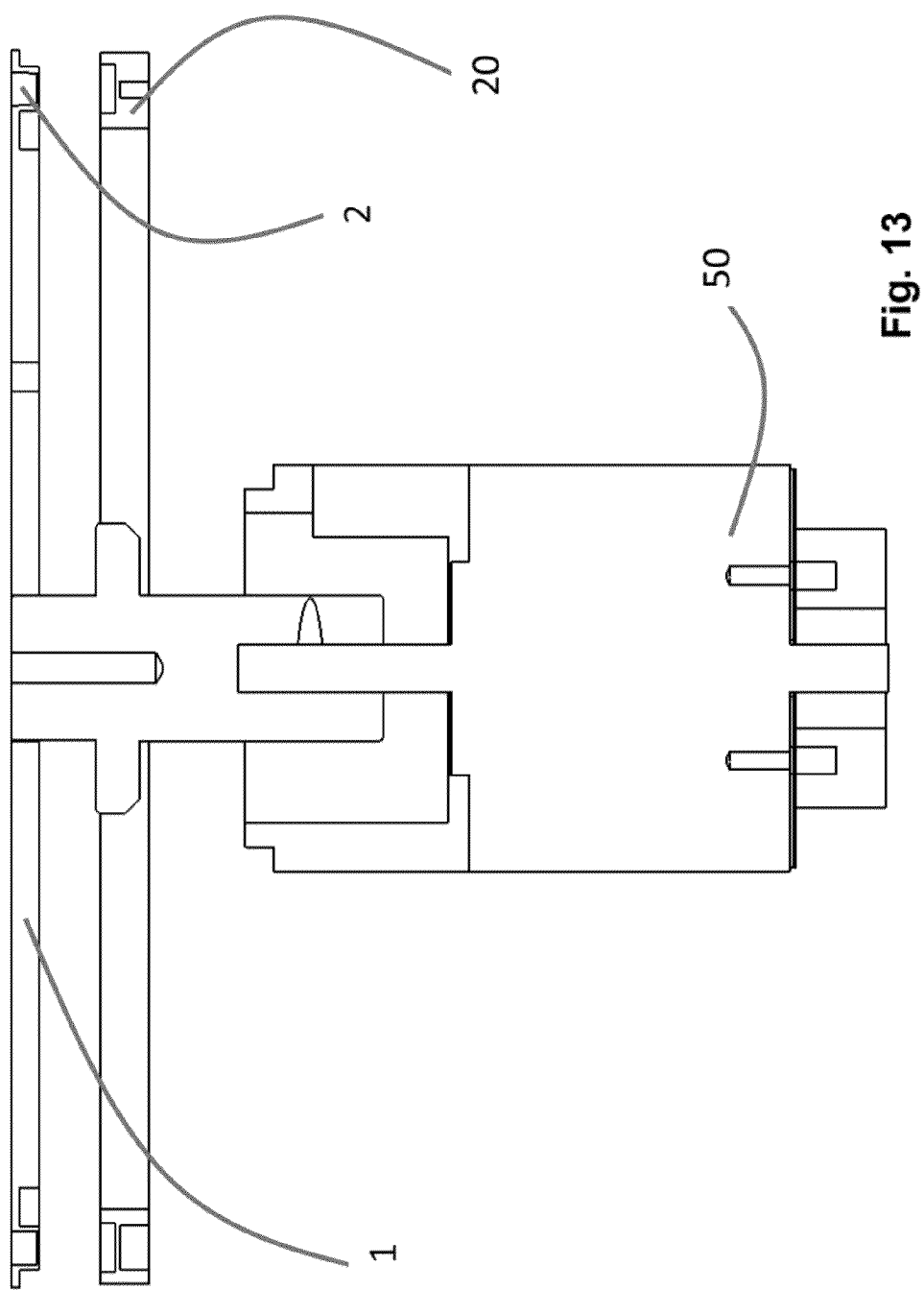
FIGS. 13 and 14 are sectional side views showing the magnetic ring (20) in first and second positions respectively.
Figure 14:
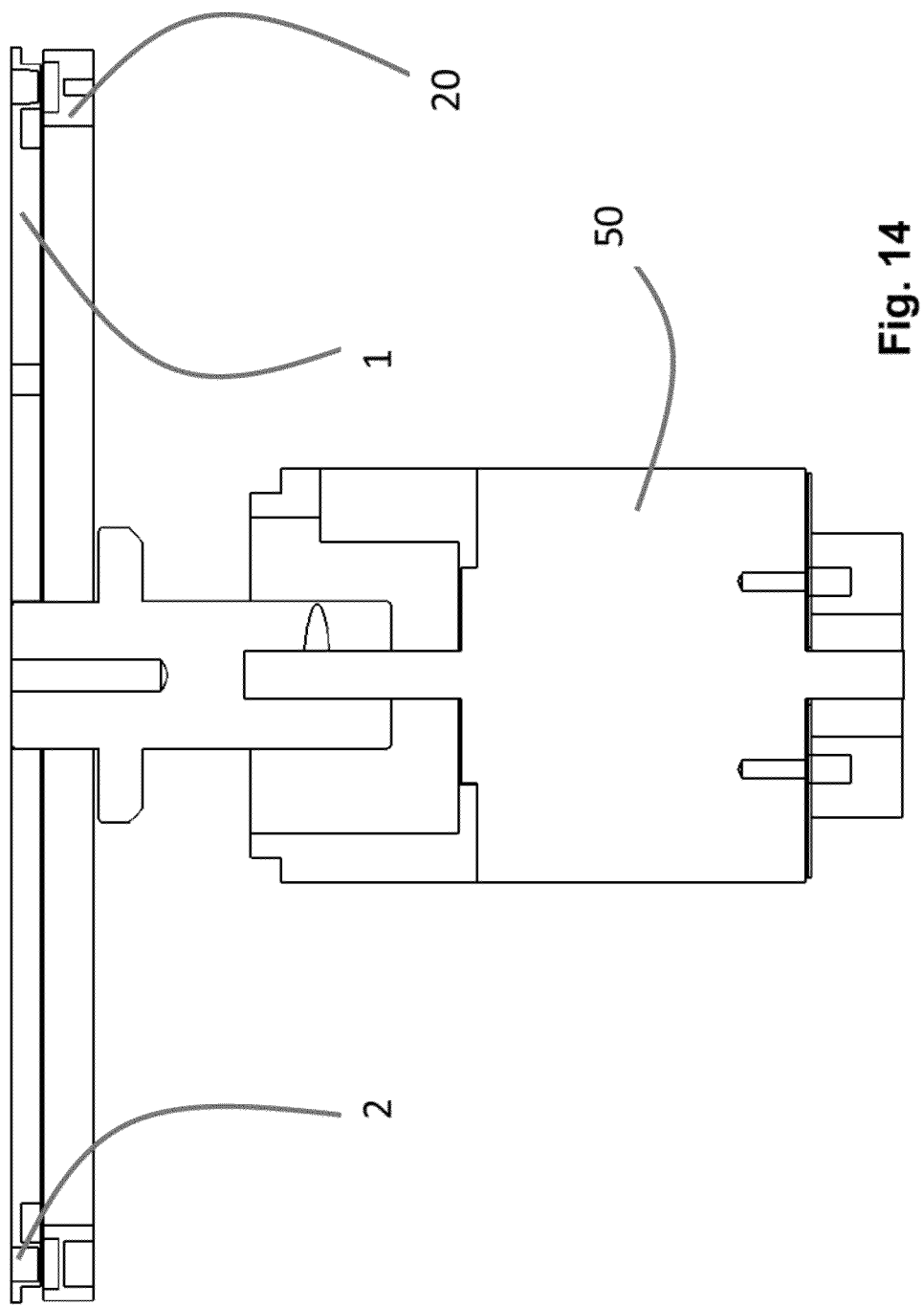

FIGS. 13 and 14 are sectional side views showing the magnetic ring in first and second positions respectively. In the second position the ring is positioned sufficiently close to the platform to exert a magnetic force on any magnetic beads contained in the wells.

FIG. 15 is another embodiment of the invention, and shows a platform having wells which are configured and arranged such that under rotation the beads spin into a cavity and the waste fluid is driven by centrifugal force through a frit or similar filter.

As discussed above, the determination of a DNA sequence can be achieved through the use of the Pyrosequencing application (see Agah A., Aghajan M., Mashayekhi F., Amini S., Davis R., Plummer J. D., Ronaghi M., Griffin P. B., *A multi-enzyme model for pyrosequencing, Nucleic Acids Res.,* 2004; 32: e166). Sequencing is achieved by detecting the release of pyrophosphate following the incorporation of a complementary three prime deoxyribonucleoside five prime triphosphate (dNTP) into a single stranded template by the DNA polymerase enzyme. Initially, the pyrophosphate must be converted to adenosine triphosphate (ATP) by the sulfurylase enzyme. It is the reaction of ATP with luciferin through the luciferase enzyme that generates a light signal, indicating the incorporation of the nucleotide and hence, the sequence of the template strand. To allow for the incorporation and detection of the next nucleotide without interference from the previously added nucleotide, the apyrase enzyme is used. Apyrase will degrade excess nucleotide prior to the addition of the next nucleotide.

During the process of pyrosequencing there is an accumulation of by-products such as sulphate and diphosphate nucleotides. These by-products inhibit the enzymes resulting in a reduction in signal quality during a long sequence run. For example, inhibition of the apyrase results in a reduction in the removal of unincorporated nucleotides that leads to non-synchronised incorporation of bases and thus poor signal detection. As a result the length of sequencing using the pyrosequencing application is currently limited to no more than 60 nucleotides (see Mashayekhi F., Ronaghi M., *Analysis of read-length limiting factors in pyrosequencing chemistry, Anal. Biochem.,* 2007; 363: 275-287).

Therefore, in order to reduce the effects of by-product inhibition, and increase read length, the present invention enables the reaction components to be washed away after a number of nucleotide exposures, allowing fresh reagent to be added to continue the next section of the sequence, while ensuring the template remains bound to the support.

Whereas this invention is illustrated and described with reference to embodiments presently contemplated as the best modes or modes of carrying out such invention in actual practice, it is to be understood that various changes may be made in adapting the invention to different embodiments without departing from the broader inventive concepts disclosed herein and comprehended by the claims that follow.

Throughout this application, various publications, patents, and/or patent applications are referenced in order to more fully describe the state of the art to which this invention pertains. The disclosures of these publications, patents, and/or patent applications are herein incorporated by reference in their entireties to the same extent as if each independent publication, patent, and/or patent application was specifically and individually indicated to be incorporated by reference.

What is claimed is:

1. A method of pyrosequencing a polynucleotide molecule, said method comprising:
    providing a rotatable platform having at least one open well for containing at least one support surface, said well further defined as being shaped or dimensioned such that a reagent deposited therein is centrifugally removable from said open well and off said platform by sufficient rotation of said platform;
    adding at least one said support surface in the form of a magnetic particle to each said open well, wherein said magnetic particle is adapted to immobilise a polynucleotide molecule or has immobilised thereon a polynucleotide molecule;
    optionally immobilising a polynucleotide molecule on said magnetic particle;
    annealing an oligonucleotide primer to a single strand of said polynucleotide molecule;
    dispensing into each said open well from a point external of said platform a series of pyrosequencing reagents, wherein after one or more dispensing steps said platform is rotated sufficiently such that any residual or unreacted said reagent is substantially centrifugally removed from each said open well and off said platform, wherein during rotation each said magnetic particle is magnetically held within each said open well;
    assaying for the presence of a pyrophosphate group in each said well; and
    repeating said dispensing and assaying steps, thereby sequencing said polynucleotide molecule.

2. A method according to claim 1 further comprising the step of positioning a magnet sufficiently close to said rotatable platform to magnetically hold said magnetic particle(s) within said open well(s) during rotation of said platform.

3. A method according to claim 2 wherein said magnet is in the form of a plate or a ring.

4. A method according to claim 3 wherein said magnetic plate or ring is further adapted to heat said open well(s) up to about 150° C. thereby heating said magnetic particle(s).

5. A method according to claim 1 further comprising the step of engaging an electromagnet to magnetically hold said magnetic particle(s) within said open well(s) during rotation of said platform.

6. A method according to claim 1 wherein said rotatable platform is substantially circular and wherein about 2 to 500 open well(s) are distributed about the periphery of said circular platform.

7. A method according to claim 6 wherein the diameter of said platform is between about 50 to 500 mm and the thickness of said platform is between about 1 to 6 mm.

8. A method according to claim 6 wherein said open wells comprise a volume of between about 0.5 to 100 μL or a well depth of about 0.5 to 5 mm, or said open wells are dimensioned to contain between about 1 to about 50 magnetic particles.

9. A method according to claim 1 wherein said rotatable platform is formed of a plastics material selected from the group consisting of polycarbonate, polystyrene, high impact polystyrene, polyethylene and polypropylene, or is formed from glass or quartz.

10. A method according to claim 1 wherein the polynucleotide molecule is chemically adsorbed or covalently or ionically, or hydrogen bonded onto each said magnetic particle, or van der Waals forces immobilise said polynucleotide molecule on each said magnetic particle.

11. A method according to claim 1 wherein said pyrosequencing reagents are selected from the group consisting of one or more of enzymes, substrates, A, T, G and/or C nucleotides or the respective suitable nucleotide analogs, washing reagents, and rinsing reagents.

12. A method according to claim 11 wherein said enzymes include one or more of DNA polymerase, ATP sulfurylase, luciferase and apyrase.

13. A method according to claim 11 wherein said substrates include adenosine 5' phosphosulfate (APS) and/or luciferin.

14. A method according to claim 1 wherein the step of rotating the rotatable platform is performed at a speed of about 400 to 1000 rpm to substantially centrifugally remove said residual or said unreacted reagent from said well(s) and further comprising the step of rotating the rotatable platform at a speed of about 10 to 200 rpm whilst dispensing said reagent.

15. A method according to claim 1 further comprising the step of vibrating said platform for thoroughly mixing together said reagent and said magnetic particle(s).

16. A method according to claim 1 wherein said polynucleotide molecule is DNA or RNA or a modified form thereof.

17. A method according to claim 1 wherein said polynucleotide molecule is biotinylated and said magnetic particle(s) comprises avidin or streptavidin or an analogue for binding the biotinylated polynucleotide molecule.

18. A method according to claim 1 wherein said dispensing of the series of pyrosequencing reagents comprises either:
 a) adding each nucleotide or its analog separately and sequentially in any desired or predetermined order, or
 b) adding A+T+G+C nucleotides or any predetermined or desired subset of these as a mixture, and optionally repeating the adding one or more times.

19. A method according to claim 1 wherein said assaying for the presence of a pyrophosphate group in each said open well comprises detecting a light signal in each said open well.

20. A method according to claim 1 wherein the polynucleotide molecule is a double stranded polynucleotide molecule and the method further comprises denaturing the double stranded polynucleotide molecule prior to the annealing.

21. A method according to claim 20 wherein said denaturing comprises heating said double stranded polynucleotide molecule to effect denaturing, or exposing said double stranded polynucleotide molecule to elevated pH.

22. A method according to claim 1 further comprising the step of washing said open well(s) with a wash reagent and optionally an enzymatic treatment.

23. A method according to claim 22 wherein said washing step occurs after one or more dispensing steps.

* * * * *

SEQUENCE LISTING

```
<160> NUMBER OF SEQ ID NOS: 6

<210> SEQ ID NO 1
<211> LENGTH: 60
<212> TYPE: DNA
<213> ORGANISM: Artificial Sequence
<220> FEATURE:
<223> OTHER INFORMATION: Chemically-synthesized template sequence

<400> SEQUENCE: 1
acgtacgtac gtacgtacgt acgtacgtac gtacgtacgt acgtacgtac gtacgtacgt      60

<210> SEQ ID NO 2
<211> LENGTH: 60
<212> TYPE: DNA
<213> ORGANISM: Artificial Sequence
<220> FEATURE:
<223> OTHER INFORMATION: Chemically-synthesized template sequence

<400> SEQUENCE: 2
acgtacgtac gtacgtacgt acgtacgtac gtacgtacgt acgtacgtac gtacgtacgt      60

<210> SEQ ID NO 3
<211> LENGTH: 60
<212> TYPE: DNA
<213> ORGANISM: Artificial Sequence
<220> FEATURE:
<223> OTHER INFORMATION: Chemically-synthesized template sequence

<400> SEQUENCE: 3
acgtacgtac gtacgtacgt acgtacgtac gtacgtacgt acgtacgtac gtacgtacgt      60

<210> SEQ ID NO 4
<211> LENGTH: 60
<212> TYPE: DNA
<213> ORGANISM: Artificial Sequence
<220> FEATURE:
<223> OTHER INFORMATION: Chemically-synthesized template sequence
```

```
<400> SEQUENCE: 4
acgtacgtac gtacgtacgt acgtacgtac gtacgtacgt acgtacgtac gtacgtacgt    60

<210> SEQ ID NO 5
<211> LENGTH: 16
<212> TYPE: DNA
<213> ORGANISM: Artificial Sequence
<220> FEATURE:
<223> OTHER INFORMATION: Chemically-synthesized template sequence

<400> SEQUENCE: 5
acgtacgtac gtacgt                                                     16

<210> SEQ ID NO 6
<211> LENGTH: 60
<212> TYPE: DNA
<213> ORGANISM: Artificial Sequence
<220> FEATURE:
<223> OTHER INFORMATION: Chemically-synthesized template sequence

<400> SEQUENCE: 6
acgtacgtac gtacgtacgt acgtacgtac gtacgtacgt acgtacgtac gtacgtacgt    60
```